(12) United States Patent
Cunningham et al.

(10) Patent No.: US 7,479,404 B2
(45) Date of Patent: Jan. 20, 2009

(54) PHOTONIC CRYSTAL BIOSENSOR STRUCTURE AND FABRICATION METHOD

(75) Inventors: Brian T. Cunningham, Champaign, IL (US); Ian Block, Champaign, IL (US); Leo Li-Ying Chan, Mount Prospect, IL (US)

(73) Assignee: The Board of Trustees of the University of Illinois, Champaign, IL (US)

( * ) Notice: Subject to any disclaimer, the term of this patent is extended or adjusted under 35 U.S.C. 154(b) by 393 days.

(21) Appl. No.: 11/177,708

(22) Filed: Jul. 8, 2005

(65) Prior Publication Data

US 2007/0009968 A1 Jan. 11, 2007

(51) Int. Cl.
*H01L 21/00* (2006.01)
(52) U.S. Cl. .............................. 438/69; 438/71; 438/32
(58) Field of Classification Search .................. 438/31, 438/32, 69, 71, 72, 87
See application file for complete search history.

(56) References Cited

U.S. PATENT DOCUMENTS

| | | | |
|---|---|---|---|
| 4,815,843 A | 3/1989 | Tiefenthaler et al. ........ 356/128 | |
| 5,071,248 A | 12/1991 | Tiefenthaler et al. | |
| 5,738,825 A | 4/1998 | Rudigier et al. .......... 422/82.11 | |
| 6,270,846 B1 | 8/2001 | Brinker et al. | |
| 6,395,651 B1 | 5/2002 | Smith et al. ................. 438/787 | |
| 6,870,624 B2 | 3/2005 | Hobbs et al. | |
| 6,951,715 B2 | 10/2005 | Cunningham et al. | |
| 6,990,259 B2 | 1/2006 | Cunningham | |
| 7,023,544 B2 | 4/2006 | Cunningham et al. | |
| 7,070,987 B2 | 7/2006 | Cunningham et al. | |
| 7,074,311 B1 | 7/2006 | Cunningham | |
| 7,094,595 B2 | 8/2006 | Cunningham et al. | |
| 7,101,660 B2 | 9/2006 | Cunningham et al. | |
| 7,118,710 B2 | 10/2006 | Cunningham | |
| 7,142,296 B2 | 11/2006 | Cunningham et al. | |
| 7,148,964 B2 | 12/2006 | Cunningham et al. | |
| 7,153,702 B2 | 12/2006 | Lin et al. | |
| 7,158,230 B2 | 1/2007 | Cunningham et al. | |
| 7,162,125 B1 | 1/2007 | Schulz | |
| 7,170,599 B2 | 1/2007 | Cunningham et al. | |
| 7,175,980 B2 | 2/2007 | Qiu et al. | |
| 7,197,198 B2 | 3/2007 | Schulz et al. | |
| 7,202,076 B2 | 4/2007 | Cunningham et al. | |
| 7,217,574 B2 | 5/2007 | Pien et al. | |
| 7,264,973 B2 | 9/2007 | Lin et al. | |
| 7,292,336 B2 | 11/2007 | Cunningham et al. | |
| 7,298,477 B1 | 11/2007 | Cunningham et al. | |
| 7,300,803 B2 | 11/2007 | Lin et al. | |
| 7,301,628 B2 | 11/2007 | Cunningham et al. | |
| 7,306,827 B2 | 12/2007 | Li et al. | |
| 7,309,614 B1 | 12/2007 | Baird et al. | |
| 7,312,090 B2 | 12/2007 | Lin et al. | |

(Continued)

OTHER PUBLICATIONS

Parashar et al., "Nano-replication of diffractive optical elements in sol-gel derived glasses", *Microelectronic Engineering*, 67-68 (2003) 710-719.

(Continued)

*Primary Examiner*—Kevin M Picardat
(74) *Attorney, Agent, or Firm*—McDonnell Boehnen Hulbert & Berghoff LLP

(57) ABSTRACT

The invention provides sensor compositions and method of making sensors.

30 Claims, 16 Drawing Sheets

U.S. PATENT DOCUMENTS

| | | | |
|---|---|---|---|
| 7,327,454 | B2 | 2/2008 | Cunningham et al. |
| 2002/0127565 | A1 | 9/2002 | Cunningham et al. .......... 435/6 |
| 2002/0168295 | A1 | 11/2002 | Cunningham et al. .... 422/82.05 |
| 2003/0017580 | A1 | 1/2003 | Cunningham et al. .... 435/287.2 |
| 2003/0017581 | A1 | 1/2003 | Li et al. .................... 435/287.2 |
| 2003/0026891 | A1 | 2/2003 | Qiu et al. ....................... 427/58 |
| 2003/0027327 | A1 | 2/2003 | Cunningham et al. .... 435/287.2 |
| 2003/0027328 | A1 | 2/2003 | Cunningham et al. .... 435/287.2 |
| 2003/0032039 | A1 | 2/2003 | Cunningham et al. .......... 435/6 |
| 2003/0059855 | A1 | 3/2003 | Cunningham et al. ........ 435/7.9 |
| 2003/0068657 | A1 | 4/2003 | Lin et al. ..................... 435/7.9 |
| 2003/0077660 | A1 | 4/2003 | Pien et al. .................... 435/7.1 |
| 2003/0092075 | A1 | 5/2003 | Pepper ........................ 435/7.9 |
| 2003/0113766 | A1 | 6/2003 | Pepper et al. .................... 435/6 |
| 2004/0132172 | A1 | 7/2004 | Cunningham et al. .... 435/287.2 |
| 2004/0132214 | A1 | 7/2004 | Lin et al. .................... 436/518 |
| 2004/0151626 | A1 | 8/2004 | Cunningham et al. ......... 422/58 |
| 2005/0227374 | A1 | 10/2005 | Cunningham et al. |
| 2006/0030033 | A1 | 2/2006 | Cunningham et al. |
| 2006/0040376 | A1 | 2/2006 | Cunningham et al. |
| 2006/0057707 | A1 | 3/2006 | Cunningham et al. |
| 2006/0286663 | A1 | 12/2006 | Cunningham et al. |
| 2007/0009380 | A1 | 1/2007 | Cunningham |
| 2007/0047874 | A1 | 3/2007 | Schulz |
| 2007/0141231 | A1 | 6/2007 | Qiu et al. |
| 2007/0172894 | A1 | 7/2007 | Genick et al. |
| 2008/0014632 | A1 | 1/2008 | Cunningham et al. |
| 2008/0020480 | A1 | 1/2008 | Lin et al. |
| 2008/0052006 | A1 | 2/2008 | Pien et al. |

OTHER PUBLICATIONS

Beck et al., "Improving stamps for 10 nm level wafer scale nanoimprint lithography", *Microelectronic Engineering*, 61-62 (2002) 441-448.

Picart et al., "Determination of structural parameters characterizing thin films by optical methods: A comparison between scanning angle reflectometry and optical waveguide lightmode spectroscopy", *Journal of Chemical Physics*, vol. 115, No. 2, 1086-1094 (2001).

Richman et al., "The binding of staphylococcal protein by the sera of different animal species", *The Journal of Immunology*, vol. 128, No. 5, 2300-2305 (1982).

Cunningham, et al., "Label-Free Assays on the BIND System", *Journal of Biomolecular Screening*, 9(6); 2004, p. 481-490.

Cunningham, et al., "Enhancing the surface sensitivity of colorimetric resonant optical biosensors", *Sensors and Actuators B*, 87 (2002) 365-370.

Li et al., "A new method for label-free imaging of biomolecular interactions", *Sensors and Actuators B*, 99 (2004) 6-13.

Lin et al., "A label-free biosensor-based cell attachment assay for characterization of cell surface molecules", *Sensors and Actuators B*, (2005) Article in Press.

Cunningham et al., "A plastic colorimetric resonant optical biosensor for multiparallel detection of label-free biochemical interactions", *Sensors and Actuators B*, 85 (2002) 219-226.

Cunningham, et al., "Colorimetric resonant reflection as a direct biochemical assay technique", *Sensors and Actuators B*, 81 (2002) 316-328.

Peng et al., "Resonant scattering from two-dimensional gratings", *J. Opt. Soc. Am. A*, vol. 13, No. 5, p. 993-1005.

Magnusson et al., "New principle for optical filters", *App. Phys. Lett.*, 61 (9), p. 1022-1024 (1992).

Peng et al., "Experimental demonstration of resonant anomalies in diffraction from two-dimensional gratings", *Optics Letters*, vol. 21, No. 8, p. 549-551 (1996).

Leatherbarrow et al., "Analysis of molecular recognition using optical biosensors", *Current Opinion in Chemical Biology*, 1999, 3:544-547.

Flannery, et al. "Characterization of thin-film aerogel porosity and stiffness with laser-generated surface acoustic waves", Thin Solid Films 388 (2000) 1-4.

International Search Report and Written Opinion issued in corresponding PCT application, application No. PCT/US2006/025400 dated Feb. 6, 2007.

Office Action dated Jan. 15, 2008 for U.S. Appl. No. 11/177,707.

PHOTONIC CRYSTAL BIOSENSOR STRUCTURE AND FABRICATION METHOD

GOVERNMENT INTERESTS

This invention was made with Government support under Grant Number BES04-27657 awarded by the National Science Foundation. The Government has certain rights in the invention.

BACKGROUND OF THE INVENTION:

Label-free optical sensors based upon surface structured photonic crystals have recently been demonstrated as a highly sensitive method for performing a wide variety of biochemical and cell-based assays. See, e.g., Cunningham, et al., *Label-Free Assays on the BIND System*. Journal of Biomolecular Screening, 2004. 9:481-490. These sensors reflect only a narrow band of wavelengths when illuminated with white light at normal incidence, where positive shifts of the reflected peak wavelength value (PWV) indicate the adsorption of detected material on the sensor surface. See, e.g., Cunningham, et al., *Colorimetric resonant reflection as a direct biochemical assay technique*. Sensors and Actuators B, 2002. 81:316-328. By spatially confining incident photons at the resonant wavelength, a high optical field is generated at the sensor surface that extends a short distance into a test sample, much like an evanescent field. The high degree of spatial confinement of resonant photons within the device structure leads to a strong interaction between the structure and adsorbed biomaterial, and to the ability to perform high resolution imaging of protein and cell attachment. See, e.g., Li, et al., *A new method for label-free imaging of biomolecular interactions*. Sensors and Actuators B, 2004. 99:6-13.

Previously, photonic crystal optical biosensors have been fabricated from continuous sheets of plastic film using a process in which the periodic surface structure is replicated from a silicon master wafer using a UV-cured polymer material. See, e.g., Cunningham, et al., *A plastic calorimetric resonant optical biosensor for multiparallel detection of label-free biochemical interactions*. Sensors and Actuators B, 2002. 85:219-226. This patterned polymer can be subsequently coated with a high refractive index $TiO_2$ layer that is generally thinner than the height of the surface structure. Such devices have been demonstrated for a wide variety of biochemical and cell-based assays, with a mass density sensitivity resolution less than 0.1 $pg/mm^2$ and a large dynamic range enabling single cell detection. See, e.g., Lin et al., *A label-free biosensor-based cell attachment assay for characterization of cell surface molecules*. Sensors and Actuators B, Accepted April 2005. In general, optimization of device sensitivity requires increasing the interaction of the electromagnetic field intensity distribution with the molecules deposited atop the photonic crystal surface. Therefore, selection of optical materials and design of the surface structure topology is aimed at extending the electromagnetic field profile from the interior regions of the photonic crystal (where they cannot interact with adsorbed material) to the region adjacent to the photonic crystal that includes the liquid test sample.

Methods are needed in the art to increase the sensitivity of these and other types of sensors and to decrease the cost of their manufacture.

SUMMARY OF THE INVENTION

One embodiment of the invention provides a method of making a sensor. The method comprises putting a liquid elastomer into a sub-wavelength period grating structure mold and curing the liquid elastomer to a form a negative mold; removing the negative mold from the mold; setting the negative mold into an uncured nanoporous film, wherein the uncured nanoporous film is supported by a substrate; allowing the nanoporous film to fully cure, partially cure or not cure; removing the negative mold from the fully cured, partially cured, or uncured nanoporous film; depositing a high dielectric constant dielectric material onto the fully cured, partially cured, or uncured nanoporous film, wherein a sensor is formed. The nanoporous film can comprise porous silica xerogel, porous aerogels, porous hydrogen silsesquioxane, a B staged polymer, porous methyl silsesquioxane, porous poly (arylene ether), or combinations thereof. The substrate can comprise plastic, epoxy, or glass. The high dielectric constant dielectric material can be tin oxide, tantalum pentoxide, zinc sulfide, titanium dioxide, silicon nitride, or a combination thereof. The refractive index of the high dielectric constant dielectric material can be from about 1.8 to about 3.0. The method can further comprise depositing a cover layer on the high dielectric constant dielectric material. The method can further comprise immobilizing one or more specific binding substances on the surface of the high dielectric constant dielectric material. The method can further comprise immobilizing one or more specific binding substances on the surface of the cover layer. The one or more specific binding substances can be detection label-free. The refractive index of the porous film can be from about 1.1 to about 2.2. The refractive index of the porous film can be from about 1.1 to about 1.5. The period of the sub-wavelength period grating structure can be from about 200 nm to about 1,500 nm and the depth of the sub-wavelength period grating structure can be from about 50 nm to about 900 nm. The refractive index of the substrate can be about 1.4 to about 1.6. The thickness of the high dielectric constant dielectric material can be about 30 nm to about 700 nm and the thickness of the nanoporous material can be about 10 mn to about 5,000 nm.

Another embodiment of the invention provides a method of making a sensor. The method comprises curing a layer of nanoporous material having a low refractive index onto a substrate; depositing a high dielectric constant dielectric material on top of the nanoporous material; and patterning the high dielectric constant dielectric material into a grating. The nanoporous film can comprise porous silica xerogel, porous aerogels, porous hydrogen silsesquioxane, a B staged polymer, porous methyl silsesquioxane, porous poly(arylene ether), or combinations thereof. The substrate can comprise plastic, epoxy, or glass. The high dielectric constant dielectric material can be tin oxide, tantalum pentoxide, zinc sulfide, titanium dioxide, silicon nitride, or a combination thereof. The refractive index of the high dielectric constant dielectric material is about 1.8 to about 3.0. The method can further comprise depositing a cover layer on the high refractive index dielectric material. The method can further comprise immobilizing one or more specific binding substances on the surface of the high refractive index dielectric material. The method can further comprise immobilizing one or more specific binding substances on the surface of the cover layer. The one or more specific binding substances can be detection label-free. The refractive index of the nanoporous film can be from about 1.1 to about 2.2. The refractive index of the nanoporous film can be from about 1.1 to about 1.5. The period of the sub-wavelength period grating structure can be about 200 nm to about 1,500 nm and the depth of the sub-wavelength period grating structure can be about 50 nm to about 900 nm. The refractive index of the substrate can be about 1.4 to about 1.6. The thickness of the high dielectric constant dielectric material can be about 30 nm to about 700 nm and the thickness of the nanoporous material can be about 10 mn to about 5,000 nm.

Therefore, use of an extremely low refractive index material for the surface structure in sensors substantially increases detection sensitivity. Therefore, substances can be measured in test samples with 2-4× lower concentrations, molecular weights, or binding affinities than have been possible previously.

DETAILED DESCRIPTION OF THE INVENTION

Figure 1:
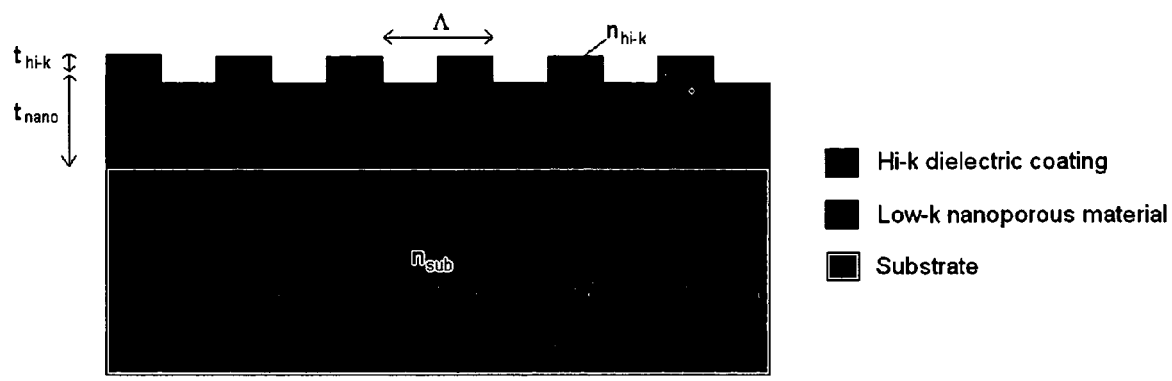
FIG. 1 shows a schematic of a nano-replicated nanoporous photonic crystal biosensor.

One embodiment of the invention provides a sensor that can be used to, inter alia, detect organic or inorganic material, such as protein, DNA, small molecules, viruses, cells, and bacteria, without the requirement of a label, such as fluorescent or radioactive labels. Photonic crystal sensors of the invention reflect only a very narrow band of wavelengths or one wavelength when illuminated with a broad wavelength light source (such as a white light or LED). The reflected color shifts to longer wavelengths in response to attachment of material to the sensor surface. Photonic crystal sensor structures of the invention provide 2-4× higher sensitivity than previously described structures. A key difference in the sensor structure that provides higher sensitivity is the replacement of a polymer sub-wavelength period grating structure with a nanoporous low refractive index material.

Methods for fabricating sensor structures that enable low cost manufacturing are also disclosed. Sensor structures of the invention have higher sensitivity than previous structures due to the use of nanoporous low refractive index material instead of a polymer sub-wavelength period grating structure. When the refractive index of the sensor structure directly beneath (and alternatively including) the sub-wavelength grating structure is reduced below the refractive index of any liquid used in a sample, the electromagnetic field of the photonic crystal interacts more strongly with the test sample, yielding a structure whose reflected wavelength is more strongly tuned by a given amount of adsorbed biological material. The system is capable of detecting, e.g., a single cell attached to its surface.

The principles of the instant invention can also be applied to, e.g., evanescent wave-based biosensors and any biosensors incorporating an optical waveguide. See, e.g., U.S. Pat. Nos. 4,815,843; 5,071,248; 5,738,825.

The sensors have utility in, inter alia, the fields of pharmaceutical research (e.g., high throughput screening, secondary screening, quality control, cytotoxicity, clinical trial evaluation), life science research (e.g., proteomics, protein interaction analysis, DNA-protein interaction analysis, enzyme-substrate interaction analysis, cell-protein interaction analysis), diagnostic tests (e.g., protein presence, cell identification), and environmental detection (bacterial and spore detection and identification). Previous patent applications and publications describe how the photonic crystal biosensor surface, in combination with a high resolution imaging instrument, can be used as a platform for performing many biochemical assays in parallel upon on single surface, using only nanoliters of sample material. See, e.g., U.S. Pat. Publ. Nos.: 2002/0168295; 2002/0127565; 2004/0132172; 2004/0151626; 2003/0027328; 2003/0027327; 2003/017581; 2003/0068657; 2003/0059855; 2003/0113766; 2003/0092075; 2003/0026891; 2003/0026891; 2003/0032039; 2003/0017580; 2003/0077660; 2004/0132214.

Photonic Crystal Sensors

A photonic crystal sensor of the invention can be used to create a sharp optical resonant reflection at a particular wavelength that can be used to track with high sensitivity the interaction of molecules, such as biological materials.

Photonic crystal sensors comprise a subwavelength structured surface. Subwavelength structured surfaces are a type of diffractive optic that can mimic the effect of thin-film coatings. See, e.g., Peng & Morris, "Resonant scattering from two-dimensional gratings," *J. Opt. Soc. Am. A*, Vol. 13, No. 5, p. 993, May 1996; Magnusson, & Wang, "New principle for optical filters," *Appl. Phys. Lett.*, 61, No. 9, p. 1022, August, 1992; Peng & Morris, "Experimental demonstration of resonant anomalies in diffraction from two-dimensional gratings," *Optics Letters*, Vol. 21, No. 8, p. 549, April, 1996. A grating of a photonic crystal sensor of the invention has a grating period that is small compared to the wavelength of incident light such that no diffractive orders other than the reflected and transmitted zeroth orders are allowed. A photonic crystal sensor can comprise a grating, which is comprised of or coated with a high dielectric constant dielectric material, sandwiched between a substrate layer and a cover layer that fills the grating grooves. Optionally, a cover layer is not used. The grating structure selectively couples light at a narrow band of wavelengths. This highly sensitive coupling condition can produce a resonant grating effect on the reflected radiation spectrum, resulting in a narrow band of reflected or transmitted wavelengths. The depth and period of the grating are less than the wavelength of the resonant grating effect.

The reflected or transmitted color of a photonic crystal sensor structure can be modified by the addition of molecules such as specific binding substances or binding partners or both to the upper surface of the cover layer or the grating surface. The added molecules increase the optical path length of incident radiation through the sensor structure, and thus modify the wavelength at which maximum reflectance or transmittance will occur.

In one embodiment, a sensor, when illuminated with white light, is designed to reflect only a single wavelength or a narrow band of wavelengths. When molecules are attached to the surface of the sensor, the reflected wavelength (color) is shifted due to the change of the optical path of light that is coupled into the grating. By immobilizing molecules, such as specific binding substances to a sensor surface, complementary binding partner molecules can be detected without the use of any kind of fluorescent probe or particle label. The detection technique can be performed with the sensor surface either immersed in fluid or dried.

When a photonic crystal sensor is illuminated with collimated white light and reflects only a narrow band of wavelengths, or a single band of wavelengths is reflected. The narrow wavelength band is described as a wavelength "peak." The "peak wavelength value" (PWV) changes when molecules are deposited or removed from the sensor surface. A readout instrument illuminates distinct locations on the sensor surface with collimated white light, and collects collimated reflected light. The collected light is gathered into a wavelength spectrometer for determination of PWV.

FIG. 1 shows a structure of a photonic crystal sensor of the invention. The sensor comprises a substrate, a patterned, low-k, nanoporous material, and a substantially uniform, high refractive index coating. The surface of the low-k nanoporous material is patterned into a sub-wavelength period grating structure onto which the high refractive index material is deposited.

In general, a low-k dielectric material of the invention has a dielectric constant, k, of about 1.1 to about 3.9. Examples of low-k dielectric materials include, for example: fluorosilicate glass (about 3.2-about 3.9); polyimides (about 3.1-about 3); hydrogen silsesquioxane (HSQ) (about 2.9-about 3.2); diamond-like carbon (about 2.7-about 3.4); black diamond (SiCOH) (about 2.7-about 3.3); parylene-N (about 2.7); B-staged polymers (CYCLOTENE™ and SiLK™) (about 2.6-about 2.7); fluorinated polyimides (about 2.5-about 2.9); methyl silsequioxane (MSQ) (about 2.6-about 2.8); poly(arylene ether) (PAE) (about 2.6-about 2.8); fluorinated DLC (about 2.4-about 2.8); parylene-F (about 2.4-about 2.5); PTFE (about 1.9); porous silica xerogels and aerogels (about 1.1-about 2.2); porous hydrogen silsesquioxane (HSQ) (about 1.7-about 2.2); porous SiLK™ (a B staged polymer) (about 1.5-about 2.0); porous methyl silsesquioxane (MSQ) (about 1.8-about 2.2); porous poly(arylene ether) (PAE) (about 1.8-about 2.2).

A low-k nanoporous material is an inorganic, porous, oxide-like low dielectric material, wherein the refractive index, n, is about 1.1 to about 2.2, and preferably about 1.1 to about 1.5. A low-k nanoporous material can be, for example, porous silica xerogels and aerogels (about 1.1-about 2.2); porous HSQ (about 1.7-about 2.2); porous SiLK™ (a B staged polymer) (about 1.5-about 2.0); porous MSQ (about 1.8-about 2.2); porous PAE (about 1.8-about 2.2). In one embodiment of the invention the nanoporous material is NANOGLASS®, which is porous $SiO_2$. Porosity is created in the $SiO_2$ thereby reducing the dielectric constant from about 3.9 to as low as 1.9.

A material with a high refractive index, suitable for the invention includes, e.g., tin oxide, tantalum pentoxide, zinc sulfide, titanium dioxide, silicon nitride, or a combination thereof. A high k dielectric material has a refractive index of about 1.8 to about 3.0. Refractive index, n, describes the optical characteristics of a medium and is defined as the ratio of the speed of light in free space over the speed of light in the medium. A substrate can comprise, for example, glass, plastic or epoxy.

In one embodiment of the invention a sensor is defined by the following parameters:

| | |
|---|---|
| $n_{hiK}$ | About 1.8 to about 3.0 |
| $n_{nano}$ | About 1.1 to about 1.5 |
| $n_{sub}$ | About 1.4 to about 1.6 |
| $\Lambda$ | About 200 nm to about 1500 nm |
| d | About 50 nm to about 900 nm |
| $t_{hiK}$ | About 30 nm to about 700 nm |
| $t_{nano}$ | About 10 nm to about 5000 nm |

In another embodiment of the invention, the sensor structure comprises the following materials:

| | |
|---|---|
| Substrate Material | Glass |
| Nanoporous Material | Nanoglass ® (Honeywell International, Santa Clara, CA) |
| High Refractive Index Coating | $TiO_2$ | and is defined by the following parameters.

| | |
|---|---|
| $n_{hiK}$ | 2.25 |
| $n_{nano}$ | 1.17 |
| $n_{sub}$ | 1.50 |
| $\Lambda$ | 550 nm |
| d | 170 nm |
| $t_{hiK}$ | 120 nm |
| $t_{nano}$ | 600 nm |

Figure 2A:
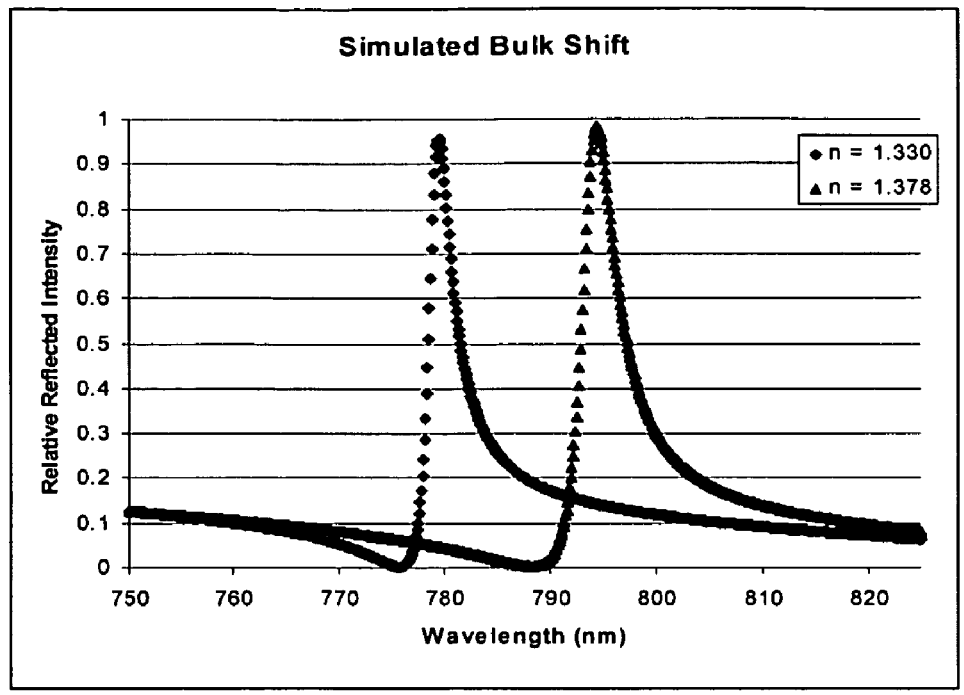
FIG. 2A-B shows (A) bulk and (B) surface shift predicted by GSolver simulations.

Simulations of the above embodiment were performed using GSolver (Grating Solver Development Co., Allen, Tex.) and FDTD Solutions (Lumerical Solutions, Inc., Vancouver, BC, Canada). The results shown in FIG. 2A predict the bulk sensitivity to be improved by more than a factor of two over that of previous designs. Bulk sensitivity is determined by the bulk shift coefficient, defined and calculated for this embodiment below.

$$\frac{\Delta PWV}{\Delta n} = \frac{\lambda_{IPA} - \lambda_{DI}}{n_{IPA} - n_{DI}} = \frac{794.4 - 779.6}{1.378 - 1.330} = 308.3 \quad (1)$$

Both simulation and experimental data for designs that do not incorporate a nanoporous material give bulk shift coefficients of approximately 150.

Figure 2B:
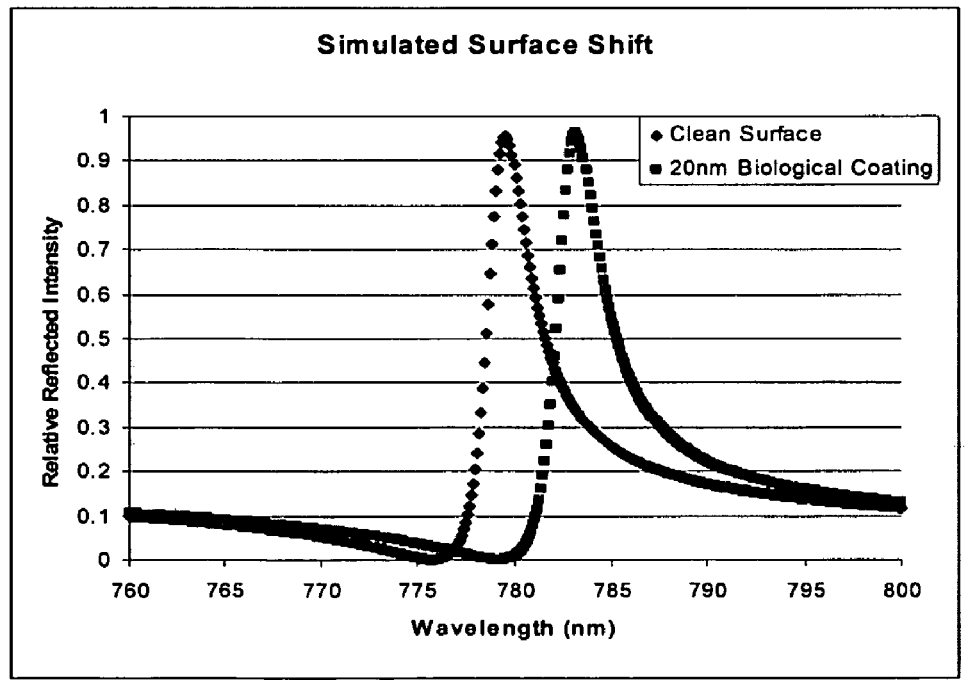

Since the proposed device functions by evanescent field interactions with materials very near the sensor surface, it is instructive to consider a refractive index shift not only of the entire bulk media but also of a thin layer atop the sensor. FIG. 2B shows GSOLVER simulation results with a 20 nm thick "biological coating" modeled by a layer with a refractive index of 1.40. While individual biological molecules or fractions of biological molecule monolayers do not have a defined refractive index value, the biological layer was modeled as a uniform thin film of defined thickness for the sake of illustration.

Figure 3A:
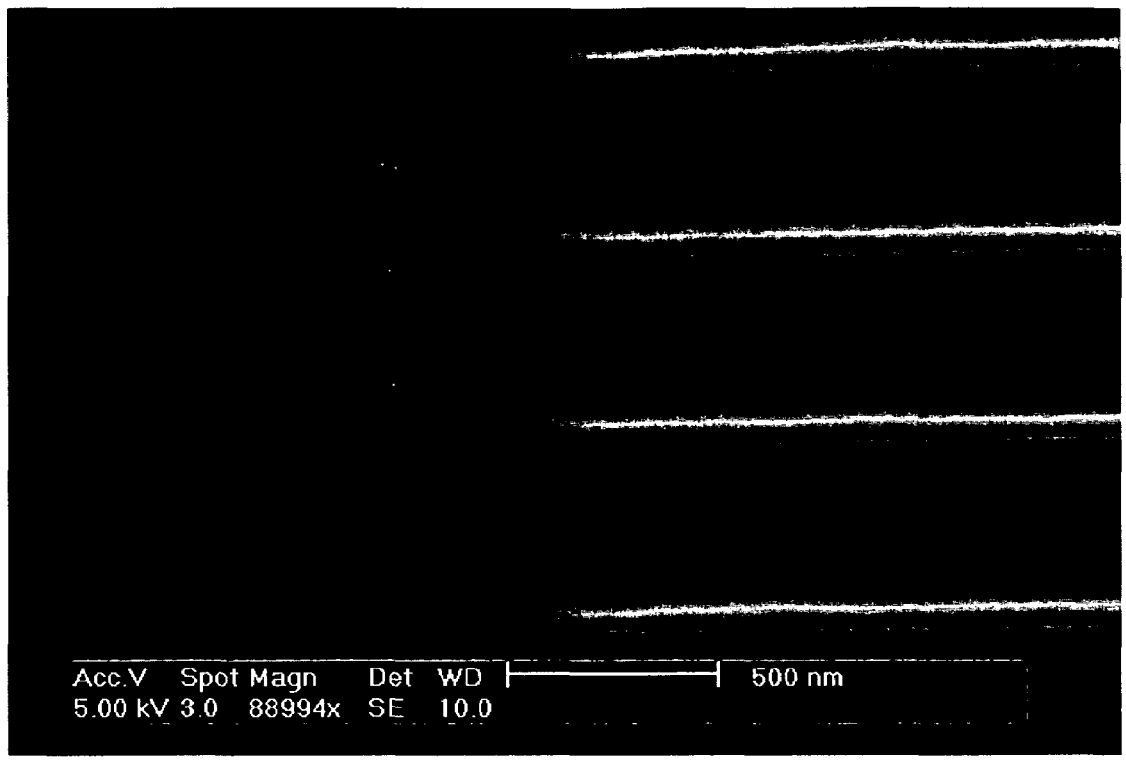
FIG. 3A-B shows SEM images of imprinted and cured periodic NANOGLASS® structure.
Figure 3B:
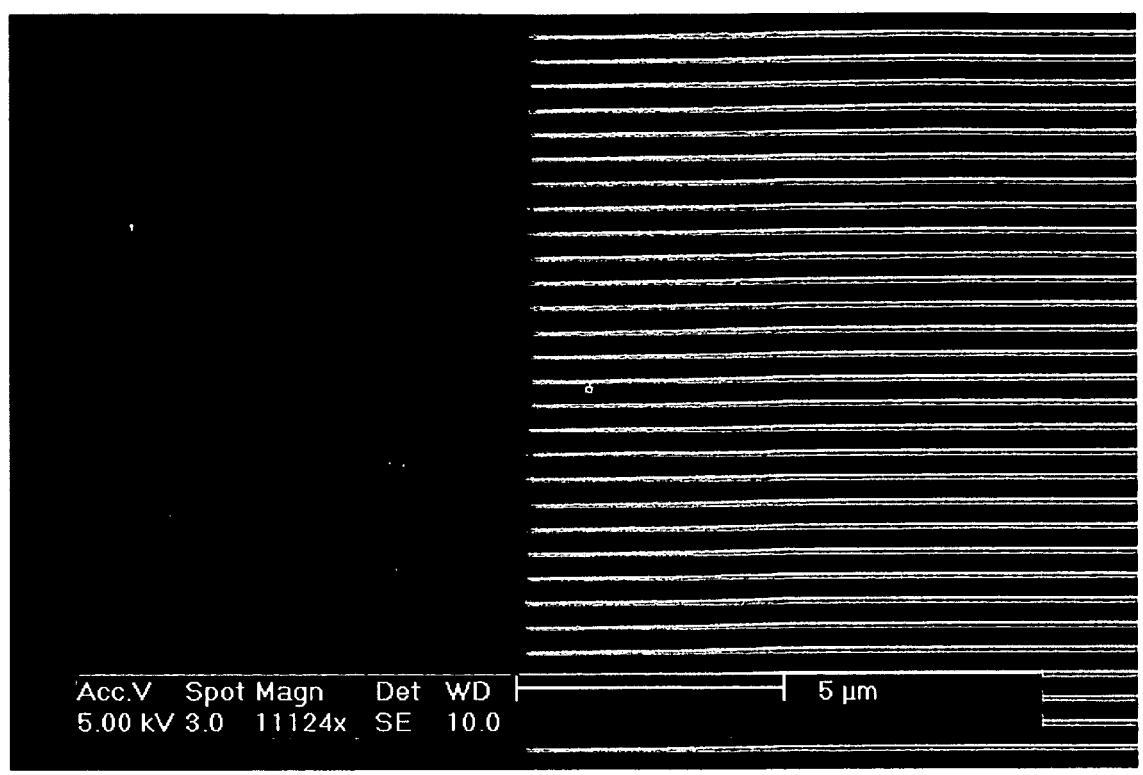
Figure 4:
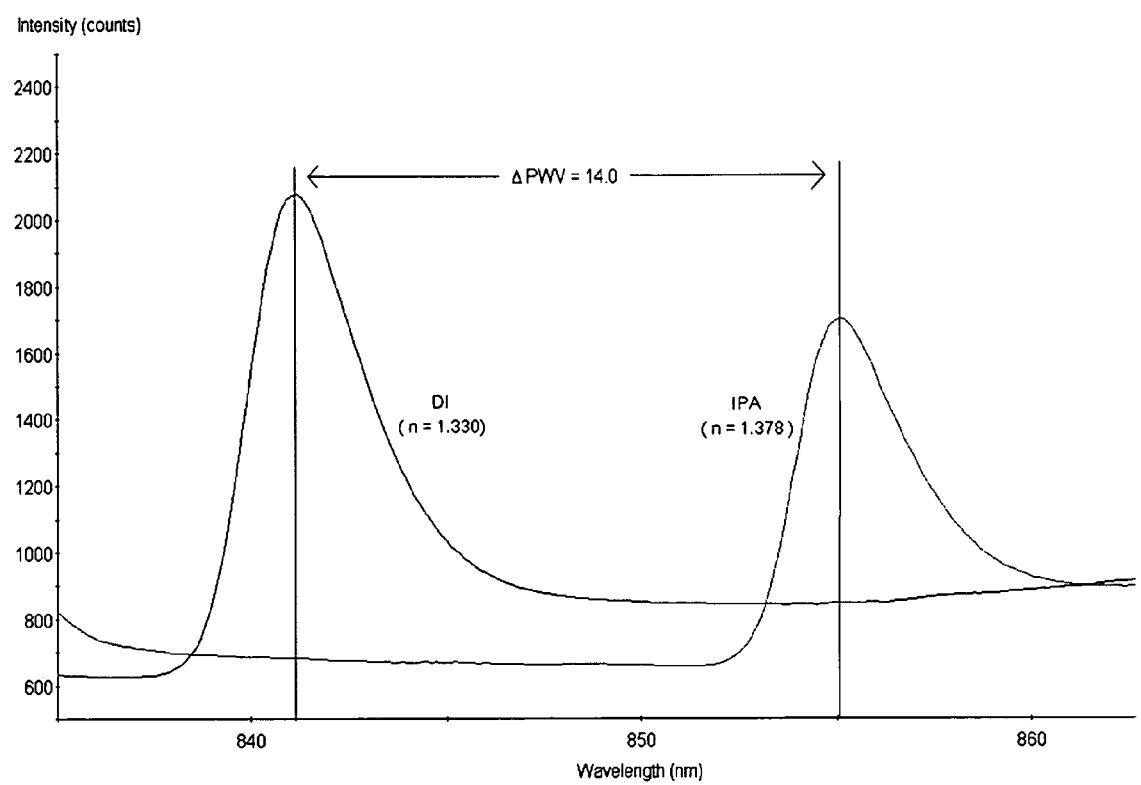
FIG. 4 shows the experimental response of nanoporous sensor under immersion in de-ionized water (DI) and isopropyl alcohol (IPA).
Figure 5A:
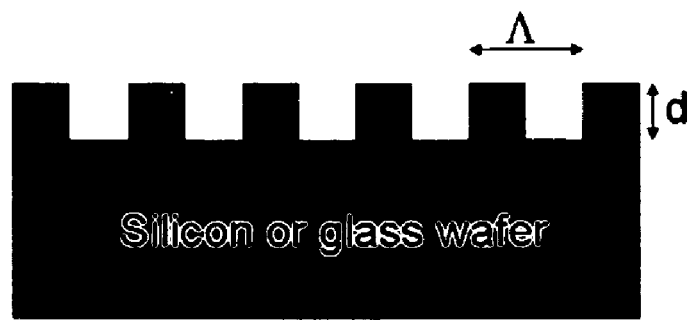
FIG. 5A-F shows process flow for nanoporous sensor fabrication.
Figure 5B:
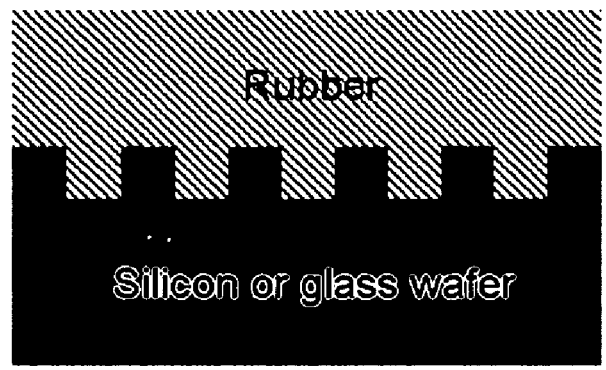
Figure 5C:
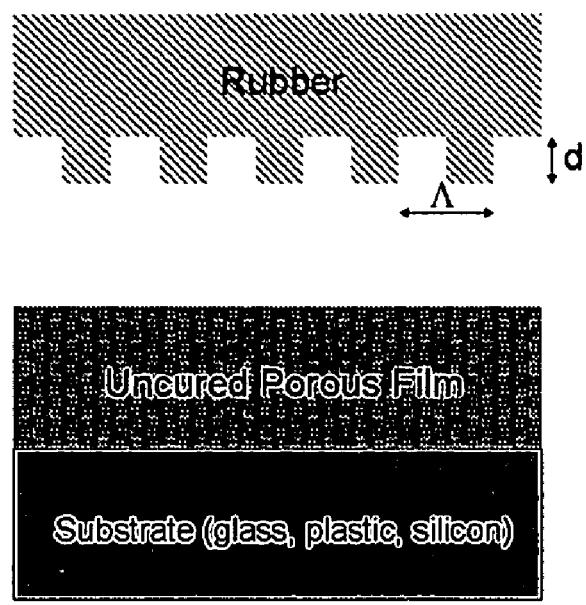
Figure 5D:
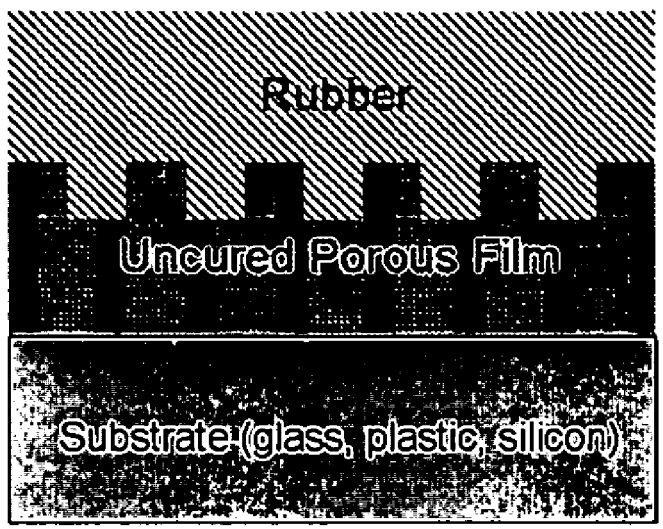
Figure 5E:
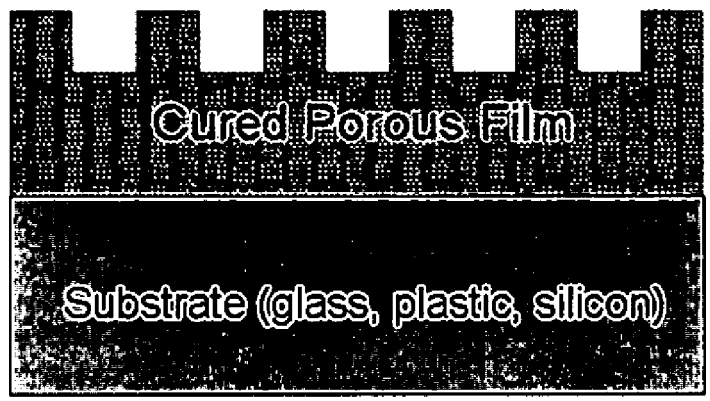
Figure 5F:
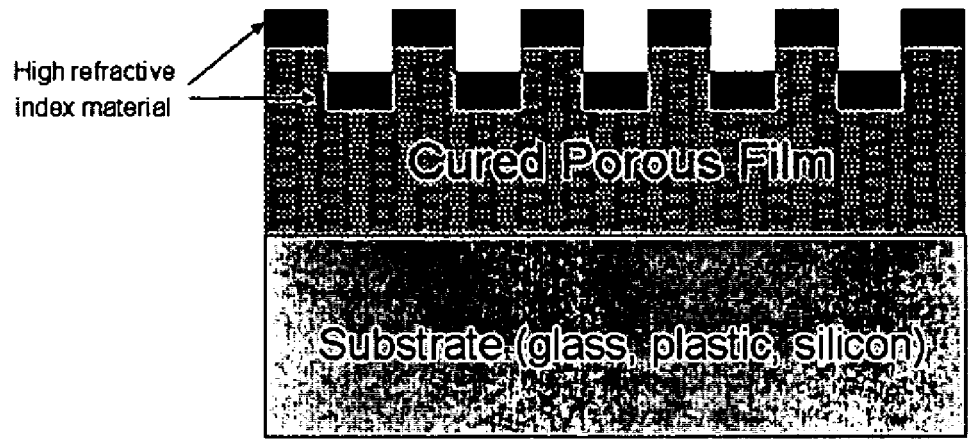

The SEM images of the patterned NANOGLASS® structure shown in FIG. 3 give evidence of a successful imprinting process. Upon deposition of $TiO_2$, the sensitivity of the completed sensor was interrogated using de-ionized water and isopropyl alcohol by examining the resulting peak wavelength (PWV) shift captured with a spectrometer on the readout instrumentation. Applying Equation 1 using the experimental data from FIG. 4, the bulk shift coefficient can be calculated as:

$$\frac{\Delta PWV}{\Delta n} = \frac{\lambda_{IPA} - \lambda_{DI}}{n_{IPA} - n_{DI}} = \frac{855.1 - 841.1}{1.378 - 1.330} = 291.7$$

which agrees to within 5% of that demonstrated though simulation.

A cross-sectional profile of a subwavelength grating can comprise any periodically repeating function, for example, a "square-wave." A grating can be comprised of a repeating pattern of shapes such as continuous parallel lines, squares, circles, ellipses, triangles, trapezoids, sinusoidal waves, ovals, rectangles, and hexagons.

A sensor can comprise a one-dimensional linear grating surface structure, i.e., a series of parallel lines or grooves. While a two-dimensional grating has features in two lateral directions across the plane of the sensor surface that are both subwavelength, the cross-section of a one-dimensional grating is only subwavelength in one lateral direction, while the long dimension can be greater than wavelength of the resonant grating effect. These include, for example, triangular or v-shaped, u-shaped, upside-down v- or u-shapes, sinusoidal, trapezoidal, stepped and square. The grating can also be sinusoidally varying in height.

An alternate sensor structure can be used that consists of a set of concentric rings. In this structure, the difference between the inside diameter and the outside diameter of each concentric ring is equal to about one-half of a grating period. Each successive ring has an inside diameter that is about one grating period greater than the inside diameter of the previous ring. The concentric ring pattern extends to cover a single sensor location—such as a microarray spot or a microtiter plate well. Each separate microarray spot or microtiter plate well has a separate concentric ring pattern centered within it. All polarization directions of such a structure have the same cross-sectional profile. The grating period of a concentric ring structure is less than the wavelength of the resonantly reflected light A sensor of the invention can further comprise a cover layer on the surface of a grating opposite to a substrate layer. Where a cover layer is present, the one or more specific binding substances are immobilized on the surface of the cover layer opposite to the grating. Preferably, a cover layer comprises a material that has a lower refractive index than a material that comprises the grating. A cover layer can be comprised of, for example, glass (including spin-on glass (SOG)), epoxy, or plastic.

Resonant reflection can also be obtained without a planarizing cover layer over the grating. Without the use of a planarizing cover layer, the surrounding medium (such as air or water) fills the grating. Therefore, molecules are immobilized to the sensor on all surfaces of a grating exposed to the molecules, rather than only on an upper surface.

The invention provides resonant reflection structures and transmission filter structures. For a resonant reflection structure, light output is measured on the same side of the structure as the illuminating light beam. For a transmission filter structure, light output is measured on the opposite side of the structure as the illuminating beam. The reflected and transmitted signals are complementary. That is, if a wavelength is strongly reflected, it is weakly transmitted. Assuming no energy is absorbed in the structure itself, the reflected+transmitted energy at any given wavelength is constant. The resonant reflection structures and transmission filters are designed to give a highly efficient reflection at a specified wavelength. Thus, a reflection filter will "pass" a narrow band of wavelengths, while a transmission filter will "cut" a narrow band of wavelengths from incident light.

In one embodiment of the invention, an optical device is provided. An optical device comprises a structure similar to any sensor of the invention; however, an optical device does not comprise one or more binding substances immobilized on the grating. An optical device can be used as a narrow band optical filter.

Evanescent wave-based sensors can comprise a waveguiding film supported by a substrate; between the waveguiding film (and optionally as part of the substrate) is a diffraction grating. See, e.g., U.S. Pat. No. 4,815,843. A low-k dielectric material, such as low-k nanoporous material can be used for the diffraction grating or the combined low-k nanoporous material and substrate. The waveguide comprises waveguiding film and the substrate. The waveguiding film can be, e.g., tin oxide, tantalum pentoxide, zinc sulfide, titanium dioxide, silicon nitride, or a combination thereof, or a polymer such as polystryrole or polycarbonate. A diffraction grating exists at the interface of the waveguiding film and the substrate or in the volume of the waveguiding film. The diffraction grating comprises a low-k material, such as low-k nanoporous material. The refractive index of the waveguiding film is higher than the index of the adjacent media (i.e., the substrate and the test sample). The substrate can be, e.g., plastic, glass or epoxy. A specific binding substance can be immobilized on the surface of the waveguiding film and a test sample added to the surface. Laser light propagates in the waveguiding film by total internal reflection. Changes in refractive index of the waveguiding film caused by molecules binding to it can be detected by observing changes in the angle of the emitted, out-coupled light.

Production of Sensors

Sensors of the invention can be produced using a flexible rubber template for embossing the grating structure into the nanoporous material while the nanoporous material is in an uncured, deformable state. Unlike nonflexible solid templates, the flexible rubber template allows solvent vapors, generated by the nanoporous material's curing process, to escape. Many flexible templates can be generated from a single silicon wafer "master" template at low cost, and a single flexible template can be used multiple times to inexpensively produce many structured nanoporous sub-wavelength grating structures.

Sensors can be produced inexpensively over large surface areas and can also be, for example, incorporated into single-use standard disposable assay liquid handling formats such as microplates, microarray slides, or microfluidic chips.

A process flow for fabricating a photonic crystal incorporating a nanoporous layer is outlined in FIG. 5. A patterned "master" wafer, usually silicon or glass, which contains features that will correspond precisely with those later imprinted into the porous film is designed (see FIG. 5A). The master is then used as a mold into which a liquid elastomer is poured, as shown in (FIG. 5B). Upon curing, the newly formed negative rubber "daughter" mold is carefully peeled away from the master. After application of the porous film to the desired substrate, the daughter mold is set atop the uncured film, e.g., as depicted in (FIG. 5D). With the mold in place, the porous material is partially cured, fully cured or not cured. The gas-permeable rubber mold allows solvent evaporation during this curing process. Once the film can sustain a rigid shape, the daughter mold is peeled away and the remaining structure is allowed to fully cure. A completed device illustrated in (FIG. 5F) is obtained by depositing a thin high refractive index material uniformly across the patterned surface of the porous film.

Figure 6:
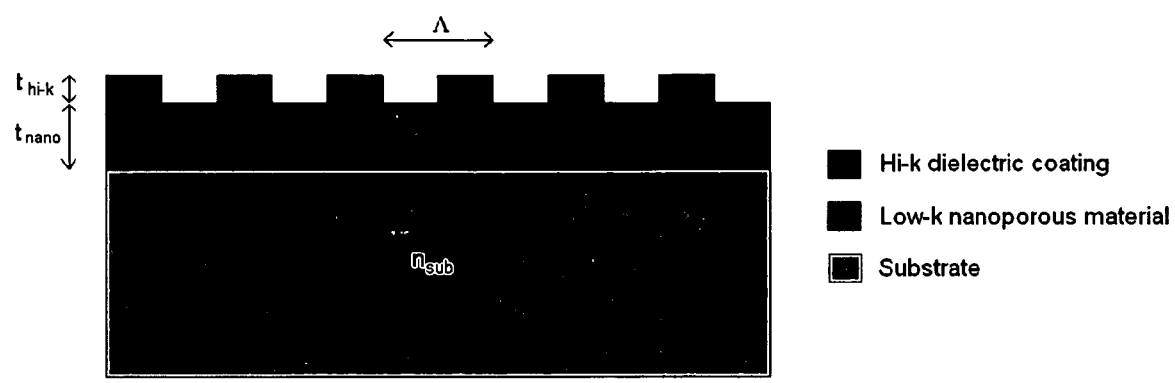
FIG. 6 shows a schematic of high dielectric constant nanoporous photonic crystal sensor.

Another approach for fabrication of a photonic crystal biosensor incorporating a nanoporous layer is illustrated in FIG. 6. With this structure, a layer of nanoporous material is cured onto a substrate. Next, a high dielectric constant material is uniformly deposited on top of the porous layer. A high dielectric constant material has a dielectric constant, k, greater than about 5% higher than the k of the nanoporous material. In one embodiment of the invention the high dielectric constant material has a k of greater than about 3.5. The deposited high-k material is then patterned by e-beam or DUV lithography, and subsequently etched to obtain the desired features. While this sensor design is not as cost effective due to the need for high-resolution lithographic processes for each device, it shows promise for obtaining sensitivity enhancements similar to those seen with the aforementioned sensor fabricated by imprinting.

Evanescent-wave based biosensors can also be made using the same processes as described herein.

Specific Binding Substances and Binding Partners

One or more specific binding substances can be immobilized on a grating or cover layer, if present, by for example, physical adsorption or by chemical binding. A specific binding substance can be, for example, an organic molecule, such as a nucleic acid, polypeptide, antigen, polyclonal antibody, monoclonal antibody, single chain antibody (scFv), F(ab) fragment, F(ab')$_2$ fragment, Fv fragment, small organic molecule, cell, virus, bacteria, polymer, peptide solutions, single- or double-stranded DNA solutions, RNA solutions, solutions containing compounds from a combinatorial chemical library, or biological sample; or an inorganic molecule. A biological sample can be for example, blood, plasma, serum, gastrointestinal secretions, homogenates of tissues or tumors, synovial fluid, feces, saliva, sputum, cyst fluid, amiotic fluid, cerebrospinal fluid, peritoneal fluid, lung lavage fluid, semen, lymphatic fluid, tears, or prostatitc fluid.

Preferably, one or more specific binding substances are arranged in a microarray of distinct locations on a sensor. One or more specific binding substances can be bound to their specific binding partners. A microarray of specific binding substances comprises one or more specific binding substances on a surface of a sensor of the invention such that a surface contains many distinct locations, each with a different specific binding substance or with a different amount of a specific binding substance. For example, an array can comprise 1, 10, 100, 1,000, 10,000, or 100,000 distinct locations. Such a sensor surface is called a microarray because one or more specific binding substances are typically laid out in a regular grid pattern in x-y coordinates. However, a microarray of the invention can comprise one or more specific binding substances laid out in any type of regular or irregular pattern. For example, distinct locations can define a microarray of spots of one or more specific binding substances. A microarray spot can be about 50 to about 500 microns in diameter. A microarray spot can also be about 150 to about 200 microns in diameter.

A microarray on a sensor of the invention can be created by placing microdroplets of one or more specific binding substances onto, for example, an x-y grid of locations on a grating or cover layer surface. When the sensor is exposed to a test sample comprising one or more binding partners, the binding partners will be preferentially attracted to distinct locations on the microarray that comprise specific binding substances that have high affinity for the binding partners. Some of the distinct locations will gather binding partners onto their surface, while other locations will not.

A specific binding substance specifically binds to a binding partner that is contacted with the surface of a sensor of the invention. A specific binding substance specifically binds to its binding partner, but does not substantially bind other binding-partners contacted with the surface of a sensor. For example, where the specific binding substance is an antibody and its binding partner is a particular antigen, the antibody specifically binds to the particular antigen, but does not substantially bind other antigens. A binding partner can be, for example, a nucleic acid, polypeptide, antigen, polyclonal antibody, monoclonal antibody, single chain antibody (scFv), F(ab) fragment, F(ab')$_2$ fragment, Fv fragment, small organic molecule, cell, virus, bacteria, polymer, peptide solutions, single- or double-stranded DNA solutions, RNA solutions, solutions containing compounds from a combinatorial chemical library, an inorganic molecule, or a biological sample.

One example of a microarray of the invention is a nucleic acid microarray, in which each distinct location within the array contains a different nucleic acid molecule. In this embodiment, the spots within the nucleic acid microarray detect complementary chemical binding with an opposing strand of a nucleic acid in a test sample.

While microtiter plates are the most common format used for biochemical assays, microarrays are increasingly seen as a means for maximizing the number of biochemical interactions that can be measured at one time while minimizing the volume of precious reagents. By application of specific binding substances with a microarray spotter onto a sensor of the invention, specific binding substance densities of 10,000 specific binding substances/in$^2$ can be obtained. By focusing an illumination beam to interrogate a single microarray location, a sensor can be used as a label-free microarray readout system.

While it is not necessary for specific binding substances or binding partners to comprise a detectable label, detectable labels can be used to detect specific binding substances or binding partners on the surface of a sensor. Where specific binding substances and binding partners of the instant invention are free of detection labels, they can still comprise other types of labels and markers for enhancement of assay sensitivity, immobilization of specific binding partners to a biosensor surface, enhancement of binding or hybridization of specific binding substances to their binding partners, and for other purposes.

Immobilization of One or More Specific Binding Substances

Molecules can be immobilized onto a sensor is so that they will not be washed away by rinsing procedures, and so that binding to molecules in a test sample is unimpeded by the sensor surface. Several different types of surface chemistry strategies have been implemented for covalent attachment of molecules to, for example, glass for use in various types of microarrays and sensors. These same methods can be readily adapted to a sensor of the invention.

One or more types of molecules can be attached to a sensor surface by physical adsorption (i.e., without the use of chemical linkers) or by chemical binding (i.e., with the use of chemical linkers). Chemical binding can generate stronger attachment of molecules on a sensor surface and provide defined orientation and conformation of the surface-bound molecules.

Other types of chemical binding include, for example, amine activation, aldehyde activation, and nickel activation. These surfaces can be used to attach several different types of chemical linkers to a sensor surface. While an amine surface can be used to attach several types of linker molecules, an aldehyde surface can be used to bind proteins directly, without an additional linker. A nickel surface can be used to bind molecules that have an incorporated histidine ("his") tag. Detection of "his-tagged" molecules with a nickel-activated surface is well known in the art (Whitesides, *Anal. Chem.* 68, 490, (1996)).

Immobilization of specific binding substances to plastic, epoxy, or high refractive index material can be performed essentially as described for immobilization to glass. However, an acid wash step can be eliminated where such a treatment would damage the material to which the specific binding substances are immobilized.

Liquid-Containing Vessels

A sensor of the invention can comprise an inner surface, for example, a bottom surface of a liquid-containing vessel. A liquid-containing vessel can be, for example, a microtiter plate well, a test tube, a petri dish, or a microfluidic channel. One embodiment of this invention is a sensor that is incorporated into any type of microtiter plate. For example, a sensor can be incorporated into the bottom surface of a microtiter plate by assembling the walls of the reaction vessels over the resonant reflection surface, so that each reaction "spot" can be exposed to a distinct test sample. Therefore, each individual microtiter plate well can act as a separate reaction vessel. Separate chemical reactions can, therefore, occur within adjacent wells without intermixing reaction fluids, and chemically-distinct test solutions can be applied-to individual wells.

The most common assay formats for pharmaceutical high-throughput screening laboratories, molecular biology research laboratories, and diagnostic assay laboratories are microtiter plates. The plates are standard-sized plastic cartridges that can contain 96, 384, or 1536 individual reaction vessels arranged in a grid. Due to the standard mechanical configuration of these plates, liquid dispensing, robotic plate handling, and detection systems are designed to work with this common format. A sensor of the invention can be incorporated into the bottom surface of a standard microtiter plate. Because the sensor surface can be fabricated in large areas, and because the readout system does not make physical contact with the sensor surface, an arbitrary number of individual sensor areas can be defined that are only limited by the focus resolution of the illumination optics and the x-y stage that scans the illumination/detection probe across the sensor surface.

A sensor can also be incorporated into other disposable laboratory assay formats, such as microarray slides, flow cells, and cell culture plates. Incorporation of a sensor into common laboratory formats is desirable for compatibility with existing microarray handling equipment such as spotters and incubation chambers.

Methods of Using Sensors

Sensors of the invention can be used, e.g., study one or a number of molecule/molecule interactions in parallel; for example, binding of one or more specific binding substances to their respective binding partners can be detected, without the use of labels, by applying one or more binding partners to a sensor that has one or more specific binding substances immobilized on its surface. A sensor is illuminated with light and a maximum in reflected wavelength, or a minimum in transmitted wavelength of light is detected from the sensor. If one or more specific binding substances have bound to their respective binding partners, then the reflected wavelength of light is shifted as compared to a situation where one or more specific binding substances have not bound to their respective binding partners. Where a sensor is coated with an array of distinct locations containing the one or more specific binding substances, then a maximum in reflected wavelength or minimum in transmitted wavelength of light is detected from each distinct location of the sensor.

In one embodiment of the invention, a variety of specific binding substances, for example, antibodies, can be immobilized in an array format onto a sensor of the invention. The sensor is then contacted with a test sample of interest comprising binding partners, such as proteins. Only the proteins that specifically bind to the antibodies immobilized on the sensor remain bound to the sensor. Such an approach is essentially a large-scale version of an enzyme-linked immunosorbent assay; however, the use of an enzyme or fluorescent label is not required.

The activity of an enzyme can be detected by detecting the reflected wavelength of light from a sensor on which one or more specific binding substances have been immobilized and applying one or more enzymes to the sensor. The sensor is washed and illuminated with light. The reflected wavelength of light is detected from the sensor. Where the one or more enzymes have altered the one or more specific binding substances of the sensor by enzymatic activity, the reflected wavelength of light is shifted.

Additionally, a test sample, for example, cell lysates containing binding partners can be applied to a sensor of the invention, followed by washing to remove unbound material. The binding partners that bind to a sensor can subsequently be eluted from the sensor and identified by, for example, mass spectrometry. Optionally, a phage DNA display library can be applied to a sensor of the invention followed by washing to remove unbound material. Individual phage particles bound to the sensor can be isolated and the inserts in these phage particles can then be sequenced to determine the identities of the binding partners.

For the above applications, and in particular proteomics applications, the ability to selectively bind material, such as binding partners from a test sample onto a sensor of the invention, followed by the ability to selectively remove bound material from a distinct location of the sensor for further analysis is advantageous. Sensors of the invention are also capable of detecting and quantifying the amount of a binding partner from a sample that is bound to a sensor array distinct location by measuring the shift in reflected wavelength of light. Additionally, the wavelength shift at one distinct sensor location can be compared to positive and negative controls at other distinct sensor locations to determine the amount of a binding partner that is bound to a sensor array distinct location.

In one embodiment of the invention, an interaction of a first molecule with a second test molecule can be detected. A sensor as described above is used; however, there are no specific binding substances immobilized on its surface. Therefore, the sensor comprises a one- or two-dimensional grating, a substrate layer that supports the one- or two-dimensional grating, and optionally, a cover layer. As described above, when the sensor is illuminated a resonant grating effect is produced on the reflected radiation spectrum, and the depth and period of the grating are less than the wavelength of the resonant grating effect.

To detect an interaction of a first molecule with a second test molecule, a mixture of the first and second molecules is applied to a distinct location on a sensor. A distinct location can be one spot or well on a sensor or can be a large area on a sensor. A mixture of the first molecule with a third control molecule is also applied to a distinct location on a sensor. The sensor can be the same sensor as described above, or can be a second sensor. If the sensor is the same sensor, a second distinct location can be used for the mixture of the first molecule and the third control molecule. Alternatively, the same distinct sensor location can be used after the first and second molecules are washed from the sensor. The third control molecule does not interact with the first molecule and is about the same size as the first molecule. A shift in the reflected wavelength of light from the distinct locations of the sensor or sensors is measured. If the shift in the reflected wavelength of light from the distinct location having the first molecule and the second test molecule is greater than the shift in the reflected wavelength from the distinct location having the first molecule and the third control molecule, then the first molecule and the second test molecule interact. Interaction can be, for example, hybridization of nucleic acid molecules, specific binding of an antibody or antibody fragment to an antigen, and binding of polypeptides. A first molecule, second test molecule, or third control molecule can be, for example, a nucleic acid, polypeptide, antigen, polyclonal antibody, monoclonal antibody, single chain antibody (scFv), F(ab) fragment, $F(ab')_2$ fragment, Fv fragment, small organic molecule, cell, virus, and bacteria.

All patents, patent applications, and other scientific or technical writings referred to anywhere herein are incorporated by reference in their entirety. The methods and compositions described herein as presently representative of preferred embodiments are exemplary and are not intended as limitations on the scope of the invention. Changes therein and other uses will be evident to those skilled in the art, and are encompassed within the spirit of the invention. The invention illustratively described herein suitably can be practiced in the absence of any element or elements, limitation or limitations that are not specifically disclosed herein. Thus, for example, in each instance herein any of the terms "comprising", "consisting essentially of", and "consisting of" can be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1

Computer Simulation

Rigorous Coupled Wave Analysis (RCWA) and Finite Difference Time Domain (FDTD) simulations were used to predict the resonant wavelength and bulk refractive index sensitivity of a one-dimensional surface photonic crystal biosensor. The device incorporates a low-index (n=1.17) nanoporous dielectric surface structure in place of the polymer (n=1.39) surface structure reported previously. A soft contact embossing method was used to create a surface-structured low-index porous film on glass substrates with a depth and period that are identical to the previous polymer structures to enable a side-by-side sensitivity comparison. The sensitivity of porous glass biosensors was compared to nonporous polymer biosensors through methods that characterize sensitivity to bulk refractive index and surface-adsorbed material. Finally, a protein binding assay comparison was performed to demonstrate sensor stability and the ability to functionalize the device for selective detection.

The polymer and porous glass sensors were modeled and simulated using two software packages. First, a 2-D diffraction grating analysis tool (GSOLVER) employing the RCWA algorithm provides a quick and simple method for initial sensor modeling. Second, FDTD (Lumerical) provides a much more versatile and powerful tool that can calculate any field component at any temporal or spectral location for an arbitrary optical device illuminated by an arbitrary source. See, e.g., Kunz & Luebbers, *The Finite Difference Time Domain Method for Electromagnetics.* 1993, Boca Raton: CRC Press. FDTD was used to verify RCWA results and to gain deeper insight into the effects of modifying the sensor structure.

Figure 8:
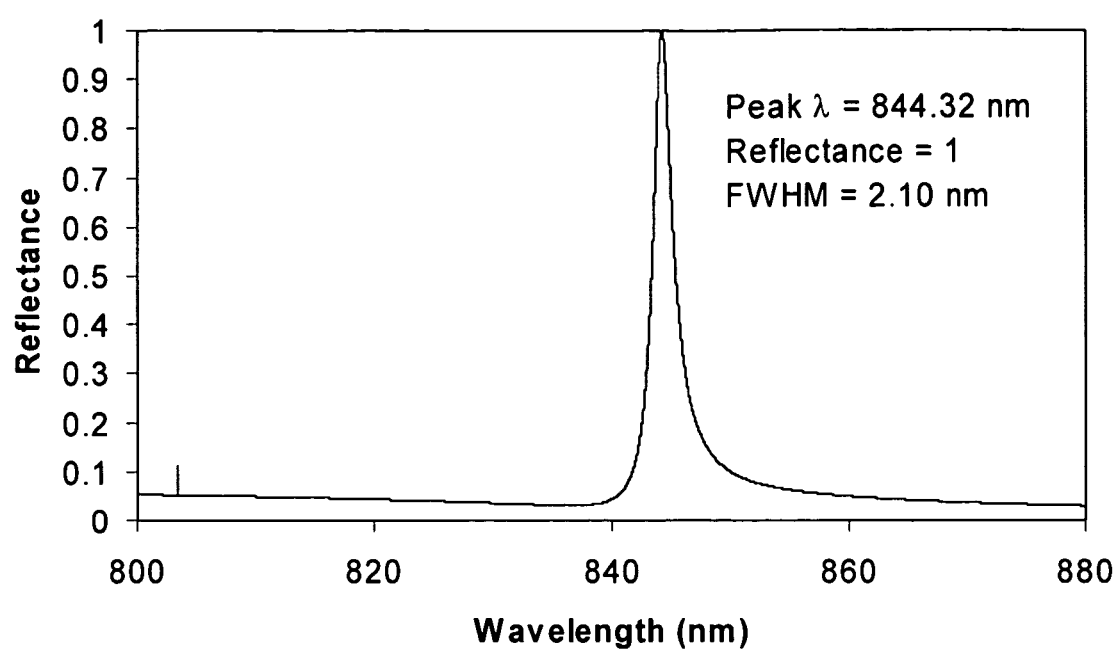
FIG. 8 shows resonant peak of porous glass sensor exposed to deionized water, as predicted by RCWA simulation.

RCWA and FDTD simulations both indicated that replacement of the patterned UV-cured polymer of previous devices with a material of lower refractive index would produce a two-fold increase in the bulk shift coefficient. The resonant wavelength of the porous glass sensor immersed in DI $H_2O$ was predicted by RCWA to be 844.3 nm with a full-width at half-maximum (FWHM) of approximately 2 nm, as shown in FIG. 8. Simulation predicts further improvements in the bulk shift coefficient with slight modifications to the sensor geometry.

Figure 9:
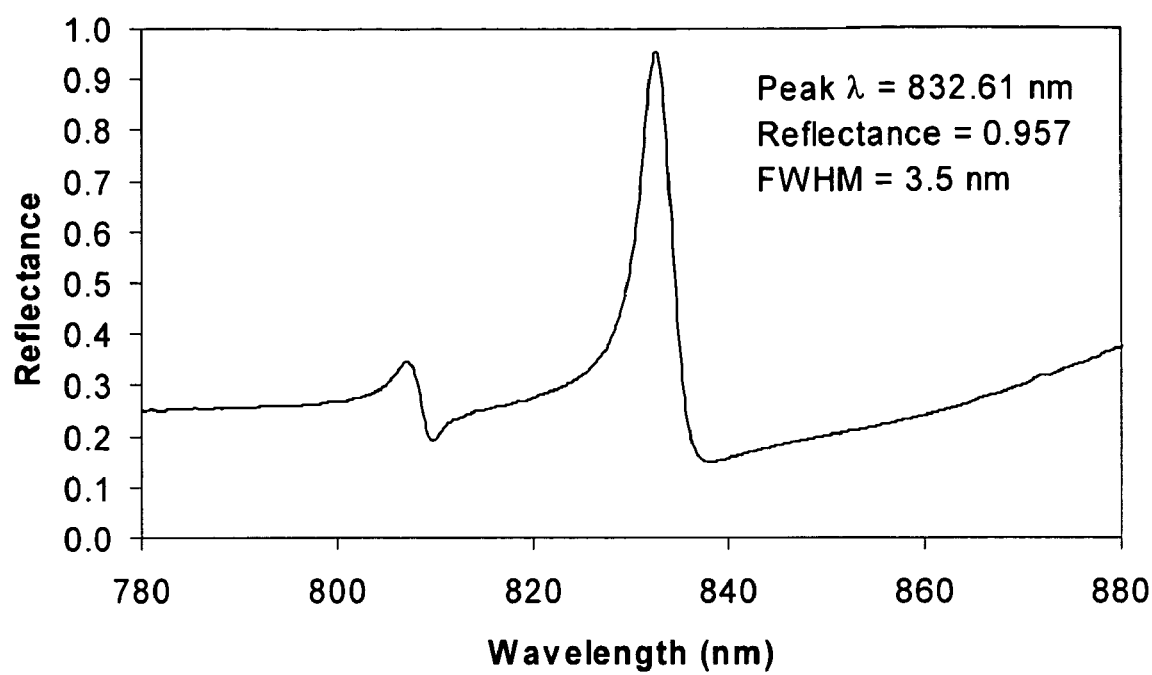
FIG. 9 shows experimentally measured resonant peak of nanoporous glass sensor immersed in deionized water.

The bulk sensitivity test using DI $H_2O$ and IPA was performed on 23 porous glass sensors and 11 polymer sensors. The average PWV shifts were 13.6±2.4 nm and 5.1±1.5 nm for the porous glass and polymer sensors, respectively. The bulk shift coefficient (ΔPWV/ΔΔ) of the porous glass sensor is measured to be 2.7±1.2 times greater than that of the polymer device. Measurements of the porous glass device in DI $H_2O$ give an average PWV of 829.5±16.5 nm and FWHM of 3.5±2.5 nm. One of the measured spectra is illustrated in FIG. 9, where the response has been normalized to a perfect reflector to account for any instrumentation losses. The lower reflection efficiency and broader FWHM measured from the replicated devices can be attributed to small but measurable material losses and to imperfections observed in the replicated structure. The large variability of measured spectral characteristics is due, at least in part, to using several slightly different (though nominally identical) master patterns and to a lack of automation of the replication process.

Example 2

Sensor Fabrication

A sol-gel derived low-index nanoporous silica thin-film (See, e.g., U.S. Pat. No. 6,395,651) was incorporated into a sensor in place of the UV-cured epoxy used in previous designs. Since the low-index material cures by heat rather than UV exposure, it was necessary to develop a new fabrication process. It was desirable to retain a low-cost imprinting method, though it was obvious that a plastic substrate could not sustain the requisite high temperatures for porous glass annealing. One possible approach to sol-gel glass imprinting was to use a polydimethylsiloxane (PDMS) mold and a glass substrate. See, e.g., Parashar, et al., *Nano-replication of diffractive optical elements in sol-gel derived glasses.* Microelectronic Engineering, 2003. 67-8: p. 710-719.

Figure 7:
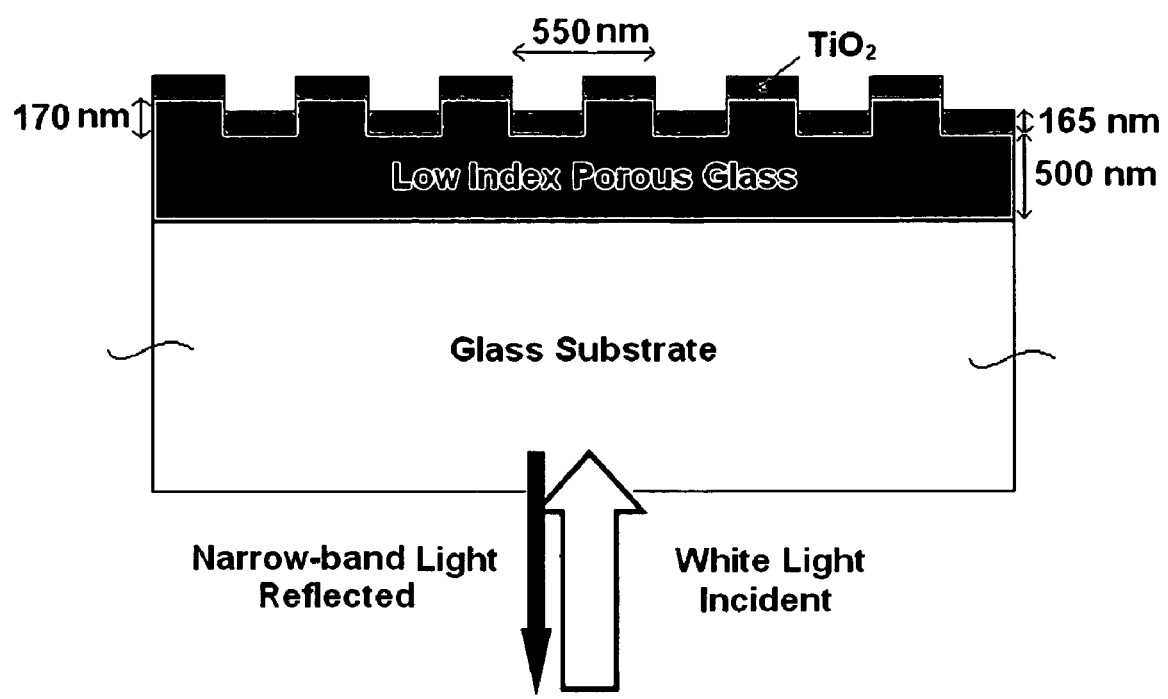
FIG. 7 shows a cross-section schematic of porous glass sensor.

The sub-wavelength grating structure of the low-k biosensor was fabricated using a combination of lithography, molding, and imprinting processes. Sylgard 184 PDMS (Dow Corning) daughter molds are first replicated from a silicon master wafer patterned with a positive image of the surface structure desired in the finished sensor. To facilitate release of the PDMS mold from the silicon wafer, the wafer was surface treated with a release layer of dimethyldichlorosilane (Repel Silane, Amersham Biosciences). See, e.g., Beck et al., *Improving stamps for 10 nm level wafer scale nanoimprint lithography.* Microelectronic Engineering, 2002. 61-2: p. 441-448. The PDMS replicas are then used to imprint a thin film of uncured NANOGLASS® (Honeywell Elec. Mat.), a low-index sol-gel glass, spun-on to a glass substrate. Once the low-index dielectric becomes rigid, the flexible PDMS mold is removed and the sol-gel glass is fully cured by further baking. The sensor structure is completed by evaporating 175 nm of $TiO_2$ onto the patterned surface. A subsequent surface treatment with dimethyldichlorosilane encourages bio-adsorption and promotes sensor stability. A schematic illustrating the cross-section of the device is shown in FIG. 7.

The polymer structure is similar to that described in a previous publication. See, e.g., Cunningham et al., *A plastic calorimetric resonant optical biosensor for multiparallel detection of label-free biochemical interactions.* Sensors and Actuators B, 2002. 85: p. 219-226. Both structures use a 550 nm period and 170 nm imprint depth, though the polyester/polymer and low-index porous glass devices use 120 nm and 165 nm $TiO_2$ coatings, respectively. The two devices will be referred to as the "polymer" and "porous glass" sensors throughout the remainder of the examples. The polymer devices were provided as an array of sensors aligned and attached to bottomless 96-well standard microtiter plates (SRU Biosystems). The porous glass devices are fabricated on 75 mm×25 mm×1 mm glass microscope slides. Adhesive rubber wells (Research International Corp.) are attached to the glass surface to provide liquid containment for 5-6 sensors on each slide.

Deionized water (DI $H_2O$, n=1.333) and Isopropyl Alcohol (IPA, n=1.378) were used to determine the bulk shift coefficient of each sensor. First, DI $H_2O$ was pipetted onto the surface of the sensor and the PWV was measured. The configuration of the readout instrument has been reported previously. See, e.g., Cunningham et al., *Colorimetric resonant reflection as a direct biochemical assay technique.* Sensors and Actuators B, 2002. 81:316-328. A broad wavelength light source was coupled to an optical fiber that illuminates a ~2 mm diameter region of the photonic crystal surface from below the substrate at normal incidence. Reflected light was collected by a second optical fiber that is bundled next to the illuminating fiber, and measured by a spectrometer. An automated motion stage enables parallel collection of reflectance data at timed intervals from many wells in order to acquire kinetic information.

Next, the surface was thoroughly dried and the previous step was repeated for IPA. The bulk shift coefficient between DI $H_2O$ and IPA was then calculated as the change in PWV divided by the change in bulk refractive index.

Example 3

PPL Bio-Adhesion Test

Sensitivity to surface-adsorbed material was characterized by the detection of a single layer film of Poly(Lys, Phe) (PPL; Sigma-Aldrich; MW=35,400 Da) prepared to a 0.5 mg/ml solution with 0.01 M phosphate buffered saline (PBS; pH =7.4) applied to the sensor surface. At a sampling interval of 1 minute, the bio-adhesion test commenced with the pipetting of PBS into the test wells. After 10 minutes, the buffer was replaced with PPL solution and was allowed to stabilize for 30 minutes. The wells were then washed three times and filled with PBS for the final 30 minutes of data acquisition.

Figure 10:
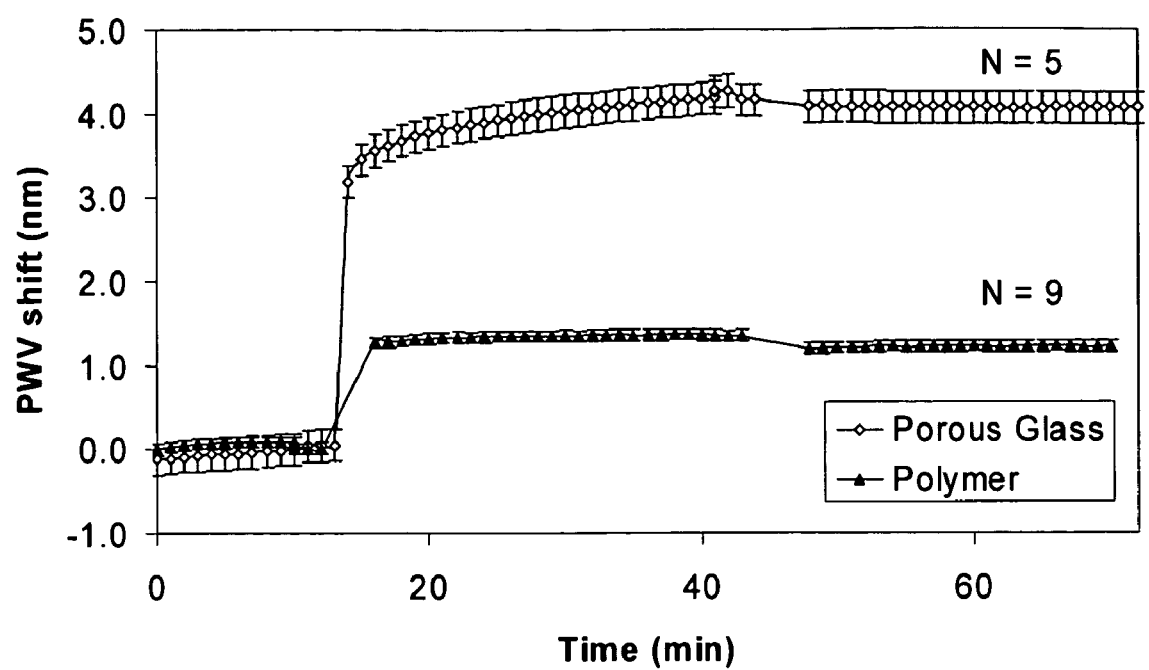
FIG. 10 shows a kinetic plot comparing PWV shifts for PPL deposited onto both porous glass and polymer sensor designs.

PPL was deposited on 5 porous glass and 9 polymer sensors. FIG. 10 compares the kinetic plots of each device, showing a ~4× increase in surface sensitivity for the porous glass sensor. The first step establishes a baseline, the second corresponds to the rapid surface adsorption and saturation of PPL, and the final third of the curve illustrates the monolayer stability after eliminating weakly or non-specifically bound molecules by rinsing with PBS buffer. The PWV shifts generated during PPL immobilization onto the porous glass sensor saturate more slowly than that measured using the polymer devices. Clearly, the porous glass sensor surface is significantly less conducive to protein monolayer adsorption. Further surface chemistry optimization should mitigate this effect. Nonetheless, the porous glass sensor exhibits excellent stability after unbound molecules are washed away.

Example 4

Multilayer Polymer Test

In order to characterize the differential sensitivity as a function of distance from the sensor surface, a series of polymer electrolyte monolayers were deposited on the sensors. By alternating between positively and negatively charged polymer layers, a stack of uniform, self-limiting polymers may be formed on the sensor while it is continuously monitored on the detection instrument. See, e.g., Cunningham et al., *Enhancing the surface sensitivity of calorimetric resonant optical biosensors.* Sensors and Actuators B, 2002. 87(2): 365-370. Three different polyelectrolytes were deposited onto the sensor surface: anionic poly(sodium 4-styrenesulfonate) (PSS; MW=70,000 Da), cationic poly(ethyleniminie) (PEI; MW=60,000 Da), and cationic poly(allylamine hydrochloride) (PAH; MW=70,000 Da). The polyelectrolytes were purchased from Sigma-Aldrich. A 0.9 M NaCl buffer solution (Sigma-Aldrich) was prepared with deionized water. The polyelectrolytes were dissolved in the buffer solution at a concentration of 5 mg/ml. At a 1 minute sampling interval, the multilayer surface sensitivity characterization was performed in 5 minute steps. First, NaCl buffer was pipetted into the sensor wells. Next, the buffer was removed and replaced by PEI solution. The wells were then washed 3 times and filled with buffer. The previous 2 steps were repeated for PSS and PAH until 7 PSS-PAH layers had been deposited atop the single PEI layer.

Figure 11:
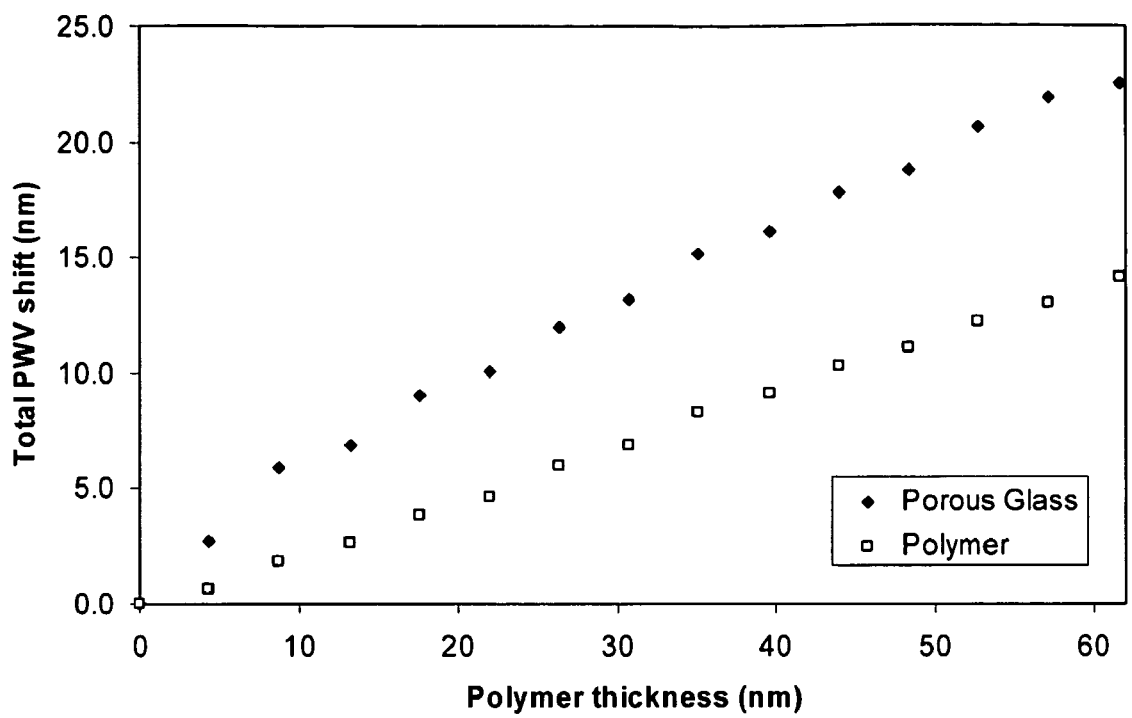
FIG. 11 shows a partial profile of PWV shift versus polymer thickness, where alternating layers of PSS and PAH contribute to the total measured shift.
Figure 12:
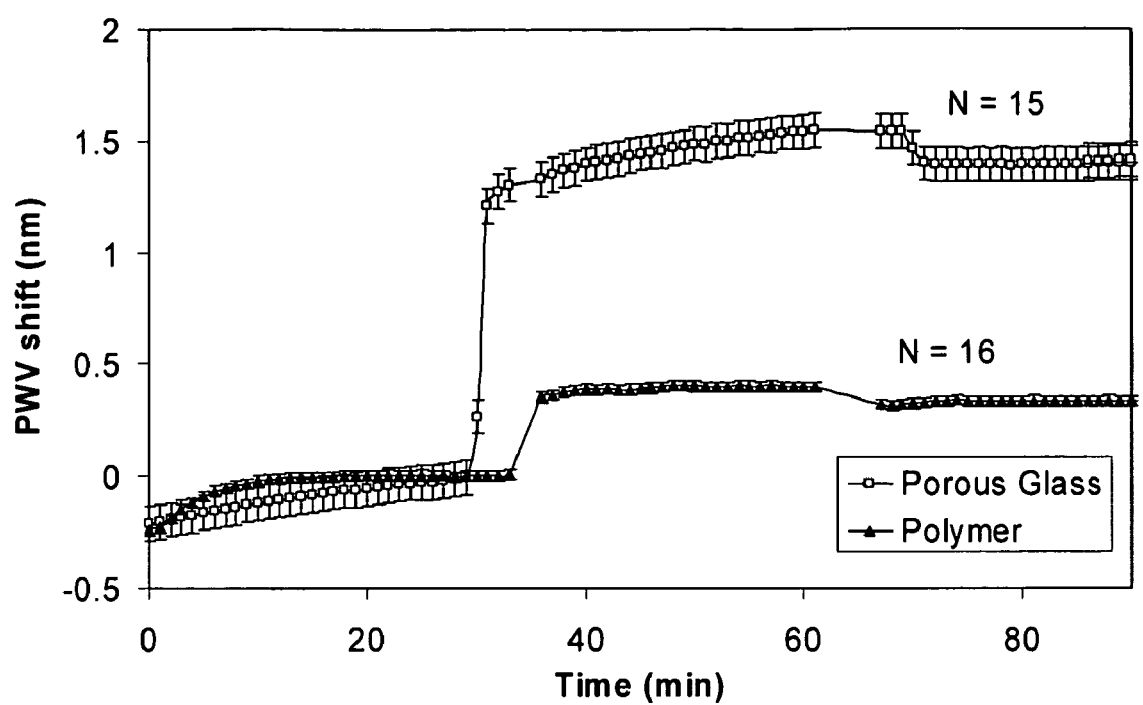
FIG. 12 shows a kinetic plot comparing PWV shifts for protein A deposited onto both porous glass and polymer sensor designs.

The 14 alternating layers of PSS and PAH described previously each cause a measurable shift in the detected PWV as they are adsorbed onto the surface. FIG. 11 gives a spatial profile of PWV shift versus polymer thickness, where each PWV shift was measured in buffer after the wash step. Each monolayer of polyelectrolyte is approximately 4.4 nm thick and has a refractive index of 1.49. See, e.g., Picart et al., *Determination of structural parameters characterizing thin* films by optical methods: A comparison between scanning angle reflectometry and optical waveguide lightmode spectroscopy. Journal of Chemical Physics, 2001. 115(2): p. 1086-1094. The porous glass sensor exhibits an average surface sensitivity ~1.5× that of the polymer sensor. However, note that each of the first 2 layers (~9 nm) deposited onto the porous glass device cause a PWV shift with twice the magnitude of each of the remaining layers, while no such effect is observed for the polymer device.

Example 5

Bioassay: Protein A—IgG

To demonstrate selective detection by the proposed device, a bioassay was performed that characterizes the affinity of human, sheep and chicken IgG for protein A. Protein A (Pierce Biotechnology) was prepared with 0.01 M PBS to a concentration of 0.5 mg/ml. The buffer was filtered with a 0.22 μm syringe filter (Nalgene) before use. Human, sheep, and chicken immunoglobulin-G (IgG) serums (Sigma-Aldrich) were diluted in 0.01 M PBS to a concentration of 0.5 mg/ml. Allowing thirty minutes between each step and sampling at a one minute interval, PBS solution was first pipetted into the sensors wells. Next, the buffer was replaced by protein A solution. The well was then rinsed 3 times and filled with buffer. After the signal stabilized, the buffer in three of the wells was replaced by human, sheep, or chicken IgG, while the fourth was left as a reference containing only the buffer. Finally, the IgGs were removed and the wells were again rinsed and filled with PBS for the final 30 minutes of data acquisition.

Figure 13:
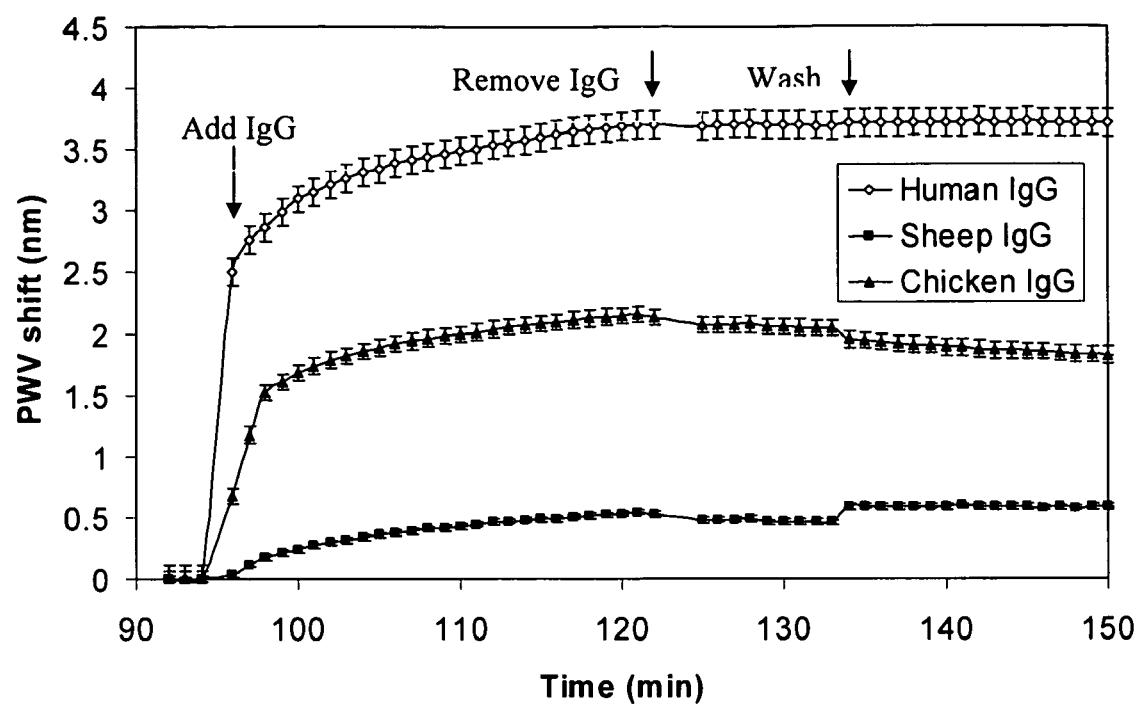
FIG. 13 shows binding kinetics of three animal IgGs to protein A measured with a nanoporous glass sensor.
Figure 14:
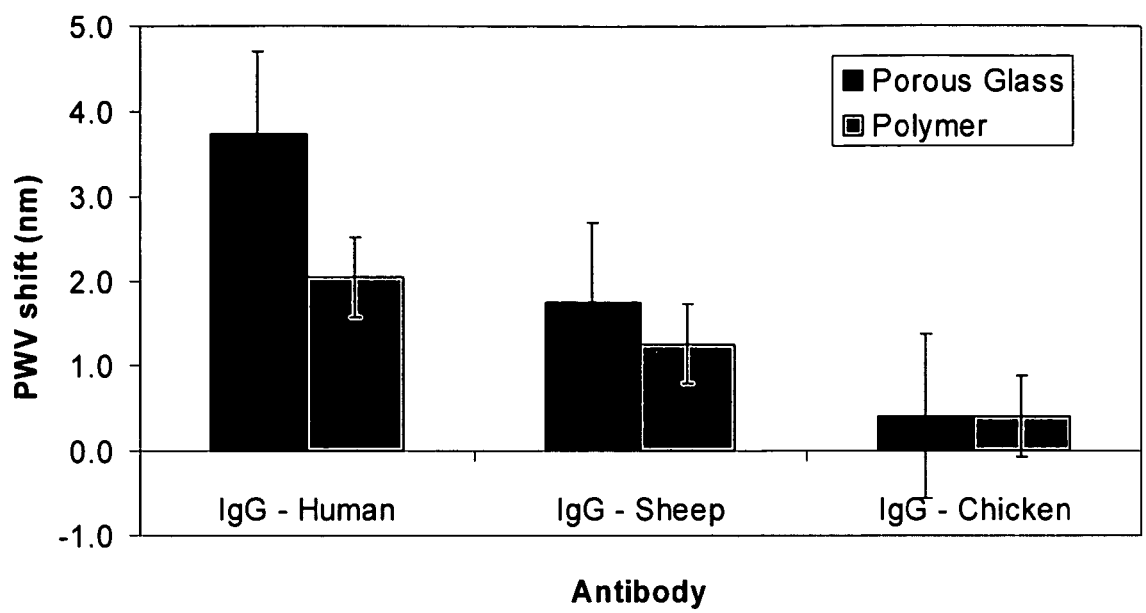
FIG. 14 shows sensor comparison of PWV shifts for each of the different IgG-protein A interactions.

Protein A was introduced into 15 porous glass and 16 polymer sensor wells. The resulting PWV shift after the wash step was ~4× greater for the porous glass devices. FIG. 13 illustrates the measured binding kinetics of human, sheep, and chicken IgG with protein A for the porous glass sensor, while FIG. 14 gives an endpoint PWV shift comparison (relative to a reference well without IgG) between the two devices for each antibody. Protein A surface adsorption saturated much more quickly on the polymer sensor surface, similar to that observed in the PPL bio-adhesion test. The porous glass device exhibits increasingly greater sensitivity for antibodies with higher affinity for protein A. Human IgG binding was detected with twice the sensitivity, while Chicken IgG, lacking any specificity for protein A (See, e.g., Richman et al., *The binding of Staphylococci protein A by the sera of different animal species*. Journal of Immunology, 1982. 128: p. 2300-2305), results in an equivalent response and provides a measure of non-specific binding.

A photonic crystal biosensor is designed to couple electromagnetic energy to biological material deposited upon its surface from a liquid test sample. While the device itself consists of a low refractive index surface structure and a high refractive index dielectric coating, the liquid test sample that fills in the surface structure must also be considered an integral part of the sensor—and the only dynamic component that can induce a change of resonant wavelength. The motivation for incorporating an extremely low refractive index material into the photonic crystal biosensor structure is to bias the electromagnetic field of the resonant wavelength to interact more strongly with the liquid test sample and less strongly with the interior regions of the photonic crystal that do not interact with surface adsorbed material.

The use of spin-on low-k dielectric materials leverages off the large investments made in the integrated circuit manufacturing community, who require rapid processing, structural stability, and exclusion of liquid penetration. A unique aspect of this work is the use of an imprinting method to accurately impart a submicron surface structure to a nanoporous glass film without the use of photolithography. The presence of the imprint tool on the surface of the low-k film during the initial stage of the curing process did not alter the refractive index of the final cured structured film. The imprinting method enables substantial cost to be incurred only in the production of the "master" silicon wafer, which is in turn used to produce a nearly unlimited number of "daughter" PDMS imprinting tools. Each PDMS tool can be used to produce a large number of sensor structures without damage to the tool because little force is needed to make the spun-on liquid low-k layer conform to the tool. After imprinting, the low-k dielectric film is cured rapidly on hotplates, using methods that are easily automated. The use of a flexible imprinting tool was found to be advantageous over imprinting from the silicon master wafer directly, as the PDMS mold was easier to release from the partially cured low-k film, and was capable of allowing permeation of volatile solvent released during the cure process. Although only 1×3-inch microscope slide regions were imprinted in the work shown here, the imprinting method can be scaled to larger surface areas to enable production of sensor areas large enough to cover an entire 96-well or 384-well standard microplate (approximately 3×5-inches).

An interesting and useful result found during comparison of porous glass sensor structures with polymer sensor structures is the disparity in sensitivity gains between bulk refractive index sensitivity and surface-adsorbed layer sensitivity. While computer models accurately predict the ~2× sensitivity increase measured for PWV shift induced by a bulk refractive index change of the solution covering the porous glass sensor surface, a ~4× increase of PWV shift was consistently measured for thin layers of adsorbed material. By measuring the PWV shift as a function of thickness using the polymer multilayer experiment (FIG. 11), we are able to characterize the strength of interaction of the coupled electromagnetic field as a function of distance away from the sensor surface. For the porous glass sensors, the interaction is particularly strong for the first few monolayers of adsorbed polymer, while the relationship between polymer thickness and PWV is highly linear for each adsorbed monolayer on the polymer sensor structure. The interaction between the test sample and the resonant electromagnetic field distribution is highly complex, as detected material can adsorb to the horizontal and vertical surfaces of the structure, where a characteristic field profile extends into the sample from each surface. Surface-based detection sensitivity is enhanced beyond the improvements in bulk sensitivity for the porous glass biosensor. Because the majority of biomolecular interactions are expected to occur within the first few nanometers from the sensor surface, the surface sensitivity is of greatest importance for increasing sensitivity in the context of surface-based biochemical assays.

We claim:
1. A method of making a sensor comprising:
 (a) putting a liquid elastomer into a sub-wavelength period grating structure mold and curing the liquid elastomer to a form a negative mold;
 (b) removing the negative mold from the mold;
 (c) setting the negative mold into an uncured nanoporous film, wherein the uncured nanoporous film is supported by a substrate;
 (d) allowing the nanoporous film to fully cure, partially cure or not cure;
 (e) removing the negative mold from the fully cured, partially cured, or uncured nanoporous film;

(f) depositing a high dielectric constant dielectric material onto the fully cured, partially cured, or uncured nanoporous film, wherein a sensor is formed.

2. The method of claim 1, wherein the nanoporous film comprises porous silica xerogel, porous aerogels, porous hydrogen silsesquioxane, a B staged polymer, porous methyl silsesquioxane, porous poly(arylene ether), or combinations thereof.

3. The method of claim 1, wherein the substrate comprises plastic, epoxy, or glass.

4. The method of claim 1, wherein the high dielectric constant dielectric material is tin oxide, tantalum pentoxide, zinc sulfide, titanium dioxide, silicon nitride, or a combination thereof.

5. The method of claim 1, wherein the refractive index of the high dielectric constant dielectric material is from about 1.8 to about 3.0.

6. The method of claim 1, further comprising depositing a cover layer on the high dielectric constant dielectric material.

7. The method of claim 1, further comprising immobilizing one or more specific binding substances on the surface of the high dielectric constant dielectric material.

8. The method of claim 6, further comprising immobilizing one or more specific binding substances on the surface of the cover layer.

9. The method of claim 7, wherein the one or more specific binding substances do not comprise a detection label.

10. The method of claim 8, wherein the one or more specific binding substances do not comprise a detection label.

11. The method of claim 1, wherein the refractive index of the nanoporous film is from about 1.1 to about 2.2.

12. The method of claim 1, wherein the refractive index of the nanoporous film is from about 1.1 to about 1.5.

13. The method of claim 1, wherein the period of the sub-wavelength period grating structure is from about 200 nm to about 1,500 nm and the depth of the sub-wavelength period grating structure is from about 50 nm to about 900 nm.

14. The method of claim 1, wherein the refractive index of the substrate is about 1.4 to about 1.6.

15. The method of claim 1, wherein the thickness of the high dielectric constant dielectric material is about 30 nm to about 700 nm and the thickness of the nanoporous film is about 10 mn to about 5,000 nm.

16. A method of making a sensor comprising:
(a) curing a layer of nanoporous material having a low refractive index onto a substrate;
(b) depositing a high dielectric constant dielectric material on top of the nanoporous material; and
(c) patterning the high dielectric constant dielectric material into a sub-wavelenth period grating structure.

17. The method of claim 16, wherein the nanoporous material comprises porous silica xerogel, porous aerogels, porous hydrogen silsesquioxane, a B staged polymer, porous methyl silsesquioxane, porous poly(arylene ether), or combinations thereof.

18. The method of claim 16, wherein the substrate comprises plastic, epoxy, or glass.

19. The method of claim 16, wherein the high dielectric constant dielectric material is tin oxide, tantalum pentoxide, zinc sulfide, titanium dioxide, silicon nitride, or a combination thereof.

20. The method of claim 16, wherein the refractive index of the high dielectric constant dielectric material is about 1.8 to about 3.0.

21. The method of claim 16, further comprising depositing a cover layer on the high refractive index dielectric material.

22. The method of claim 16, further comprising immobilizing one or more specific binding substances on the surface of the high refractive index dielectric material.

23. The method of claim 21, further comprising immobilizing one or more specific binding substances on the surface of the cover layer.

24. The method of claim 22, wherein the one or more specific binding substances do not comprise a detection label.

25. The method of claim 23, wherein the one or more specific binding substances do not comprise a detection label.

26. The method of claim 16, wherein the refractive index of the nanoporous material is from about 1.1 to about 2.2.

27. The method of claim 16, wherein the refractive index of the nanoporous material is from about 1.1 to about 1.5.

28. The method of claim 16, wherein the period of the sub-wavelength period grating structure is about 200 nm to about 1,500 nm and the depth of the sub-wavelength period grating structure is about 50 nm to about 900 nm.

29. The method of claim 16, wherein the refractive index of the substrate is about 1.4 to about 1.6.

30. The method of claim 16, wherein the thickness of the high dielectric constant dielectric material is about 30 nm to about 700 nm and the thickness of the nanoporous material is about 10 mn to about 5,000 nm.

* * * * *

UNITED STATES PATENT AND TRADEMARK OFFICE
CERTIFICATE OF CORRECTION

PATENT NO. : 7,479,404 B2
APPLICATION NO. : 11/177708
DATED : January 20, 2009
INVENTOR(S) : Cunningham et al.

It is certified that error appears in the above-identified patent and that said Letters Patent is hereby corrected as shown below:

Col. 2, Line 37, "mn" should read --nm--.

Col. 3, Line 2, "mn" should read --nm--.

Col. 19, Line 43, "mn" should read --nm--.

Col. 20, Line 4, "wavelenth" should read --wavelength--.

Col. 20, Line 44, "mn" should read --nm--.

Signed and Sealed this

Eighth Day of June, 2010

David J. Kappos
*Director of the United States Patent and Trademark Office*